(12) United States Patent
Nesvadba et al.

(10) Patent No.: US 6,518,326 B1
(45) Date of Patent: Feb. 11, 2003

(54) OPEN CHAIN ALKOXYAMINE COMPOUNDS AND THEIR USE AS POLYMERIZATION REGULATORS

(75) Inventors: Peter Nesvadba, Marly (CH); Andreas Kramer, Düdingen (CH); Marie-Odile Zink, Mulhouse (FR); Dario Lazzari, Bologna (IT)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/744,731

(22) PCT Filed: Jul. 27, 1999

(86) PCT No.: PCT/EP99/05377

§ 371 (c)(1),
(2), (4) Date: Jan. 29, 2001

(87) PCT Pub. No.: WO00/07981

PCT Pub. Date: Feb. 17, 2000

(30) Foreign Application Priority Data

Jul. 31, 1998 (EP) .............................. 98810741

(51) Int. Cl.[7] .................. C07C 239/18; C07C 239/20; C07C 239/12; C07C 239/16; C08F 291/00; C08F 291/12; C08F 2/46

(52) U.S. Cl. ........................ 522/12; 522/18; 522/39; 522/65; 522/170; 522/175; 522/177; 522/182; 522/188; 526/220; 526/217; 526/328; 526/328.5; 526/329.2; 526/329.3; 526/341; 526/346; 564/300; 564/301

(58) Field of Search ............................. 522/11, 12, 34, 522/39, 182, 18, 65, 170, 175, 177, 188; 564/300, 301; 526/220, 217, 328, 328.5, 329.2, 329.3, 341, 346

(56) References Cited

U.S. PATENT DOCUMENTS

| 3,253,015 A | | 5/1966 | Hoffmann ................ 260/465.5 |
| 5,412,047 A | * | 5/1995 | Georges et al. ............ 526/204 |
| 5,449,724 A | * | 9/1995 | Moffat et al. ................ 526/193 |
| 5,498,679 A | * | 3/1996 | Moffat et al. |
| 5,552,502 A | * | 9/1996 | Odell et al. .................. 526/234 |
| 5,610,250 A | * | 3/1997 | Veregin et al. ............. 526/204 |
| 5,677,388 A | * | 10/1997 | Koster et al. ................ 525/267 |
| 5,723,511 A | * | 3/1998 | Kazmaier et al. ........... 522/149 |
| 5,910,549 A | * | 6/1999 | Matyjaszewski et al. ... 526/217 |
| 6,087,451 A | * | 7/2000 | Georges et al. ............. 525/259 |
| 6,262,206 B1 | * | 7/2001 | Nesvadba et al. .......... 526/213 |
| 6,271,340 B1 | * | 8/2001 | Anderson et al. |
| 6,288,186 B1 | * | 9/2001 | Matyjaszewski et al. ... 526/220 |
| 6,320,007 B1 | * | 11/2001 | Kazmaier et al. |
| 6,353,107 B1 | * | 3/2002 | Kramer et al. .............. 544/180 |

FOREIGN PATENT DOCUMENTS

| EP | 0135280 | 3/1985 |
| EP | 0735052 | 10/1996 |
| FR | 1357477 | 7/1964 |

OTHER PUBLICATIONS

A. N. Boyd et al., J. Chem. Soc., 1958, pp. 2056–2058.
Chem. Abstr. vol. 64, No. 3, No. 3331h, (1966).
Chem. Abstr. vol. 86, No. 7, No. 42787t, (1977).
Chem. Abstr. vol. 69, No. 17, No. 66691g, (1968).
Chem. Abstr. vol. 97, No. 2, No. 6820s, (1982).
Chem. Abstr. vol. 67, No. 19, No. 90274c, (1967).

* cited by examiner

*Primary Examiner*—Susan W. Berman
(74) *Attorney, Agent, or Firm*—Tyler A. Stevenson

(57) ABSTRACT

The invention relates to open chain alkoxyamine compounds useful as polymerization regulators. The open chain alkoxyamine compounds are useful for the polymerization of ethylenically unsaturated monomers. The compounds of the present invention provide polymeric resin products having low polydispersity. The polymerization process proceeds with enhanced monomer to polymer conversion efficiency. In particular, this invention relates to stable free radical-mediated polymerization processes which provide homopolymers, random copolymer, block copolymers, multiblock copolymers, graft copolymers and the like, at enhanced rates of polymerization and enhanced monomer to polymer conversions.

20 Claims, No Drawings

OPEN CHAIN ALKOXYAMINE COMPOUNDS AND THEIR USE AS POLYMERIZATION REGULATORS

The present invention relates to open chain alkoxyamine compounds, a polymerizable composition comprising a) at least one ethylenically unsaturated monomer and b) at least one open chain alkoxyamine compound. Further aspects of the present invention are a process for polymerizing ethylenically unsaturated monomers, and the use of open chain alkoxyamine compounds for controlled polymerization. The intermediate N-oxyl derivatives, a composition of the N-oxyl derivatives with ethylenically unsaturated monomers and a free radical initiator X., as well as a process for polymerization are also subjects of the present invention.

The compounds of the present invention provide polymeric resin products having low polydispersity. The polymerization process proceeds with enhanced monomer to polymer conversion efficiency. In particular, this invention relates to stable free radical-mediated polymerization processes which provide homopolymers, random copolymers, block copolymers, multiblock copolymers, graft copolymers and the like, at enhanced rates of polymerization and enhanced monomer to polymer conversions.

Polymers or copolymers prepared by free radical polymerization processes inherently have broad molecular weight distributions or polydispersities which are generally higher than about four. One reason for this is that most of the free radical initiators have half lives that are relatively long, ranging from several minutes to many hours, and thus the polymeric chains are not all initiated at the same time and the initiators provide growing chains of various lengths at any time during the polymerization process. Another reason is that the propagating chains in a free radical process can react with each other in processes known as combination and disproportionation, both of which are irreversibly chain-terminating reaction processes. In doing so, chains of varying lengths are terminated at different times during the reaction process, resulting in resins consisting of polymeric chains which vary widely in length from very small to very large and which thus have broad polydispersities. If a free radical polymerization process is to be used for producing narrow molecular weight distributions, then all polymer chains must be initiated at about the same time and termination of the growing polymer-chains by combination or disproportionation processes must be avoided.

Conventional radical polymerization reaction processes pose various significant problems, such as difficulties in predicting or controlling the molecular weight, the polydispersity and the modality of the polymers produced. Furthermore, free radical polymerization processes in bulk of the prior art are difficult to control because the polymerization reaction is strongly exothermic and an efficient heat removal in the highly viscous polymer is mostly impossible. The exothermic nature of the prior art free radical polymerization processes often severely restricts the concentration of reactants or the reactor size upon scale-up.

Due to the above mentioned uncontrollable polymerization reactions, gel formation in conventional free radical polymerization processes are also possible and cause broad molecular weight distributions and/or difficulties during filtering, drying and manipulating the product resin.

U.S. Pat. No. 4,581,429 to Solomon et al., issued Apr. 8, 1986, discloses a free radical polymerization process which controls the growth of polymer chains to produce short chain or oligomeric homopolymers and copolymers, including block and graft copolymers. The process employs an initiator having the formula (in part) R'R"N—O—X, where X is a free radical species capable of polymerizing unsaturated monomers. The reactions typically have low conversion rates. Specifically mentioned radical R'R"N—O. groups are derived from 1,1,3,3 tetraethylisoindoline, 1,1,3,3 tetrapropylisoindoline, 2,2,6,6 tetramethylpiperidine, 2,2,5,5 tetramethylpyrrolidine or di-t-butylamine. However, the suggested compounds do not fulfill all requirements. Particularly the polymerization of acrylates does not proceed fast enough and/or the monomer to polymer conversion is not as high as desired.

EP-A-735 052 discloses a method for preparing thermoplastic polymers of narrow poly-dispersities by free radical-initated polymerization, which comprises adding a free radical initiator and a stable free radical agent to the monomer compound.

This method has the disadvantage that uncontrollable recombinations of initiator radicals occur immediately after their formation, thus producing variable ratios between initiator radicals and stable free radicals. Consequently there is no good control of the polymerization process.

There is therefore still a need for polymerization processes for the preparation of narrow polydispersity polymeric resins with defined molecular weights using the economical free radical polymerization techniques. These polymerization processes will also control the physical properties of the polymers such as viscosity, hardness, gel content, processability, clarity, high gloss, durability, and the like.

The polymerization processes and resin products of the present invention are useful in many applications, including a variety of specialty applications, such as for the preparation of block copolymers which are useful as compatibilizing agents for polymer blends, or dispersing agents for coating systems or for the preparation of narrow molecular weight resins or oligomers for use in coating technologies and thermoplastic films or as toner resins and liquid immersion development ink resins or ink additives used for electrophotographic imaging processes.

Surprisingly, it has now been found that it is possible to overcome the afore mentioned shortcomings of the prior art by providing a polymerizable composition containing specific initiator compounds. Polymerization of the composition results in a polymer or copolymer of narrow polydispersity and a high monomer to polymer conversion even at relatively low temperatures and at short reaction times, making the polymerization process particularly suitable for industrial applications. The resulting copolymers are of high purity and in many cases colorless, therefore not requiring any further purification.

The present invention relates to open chain alkoxyamine compounds which have no or at most only one electron withdrawing group at the C-atom in α-position to the nitrogen atom. These compounds are stable enough at low temperature and decompose readily at elevated temperature. Therefore being almost ideally suitable for controlled polymerizations.

One object of the present invention is a compound according to formula Ia, Ib or Ic

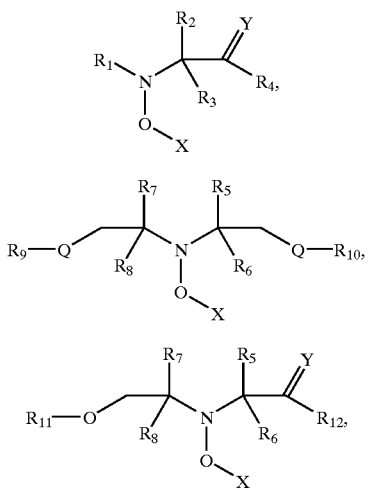

wherein

Y is O or $CH_2$;

Q is O or $NR_{20}$, wherein $R_{20}$ is hydrogen or $C_1$–$C_{18}$alkyl;

$R_1$ is tertiary $C_4$–$C_{18}$alkyl or phenyl, which are unsubstituted or substituted by halogen, OH, $COOR_{21}$ or $C(O)$—$R_{22}$ wherein $R_{21}$ is hydrogen, a alkali metal atom or $C_1$–$C_{18}$alkyl and $R_{22}$ is $C_1$–$C_{18}$alkyl; or $R_1$ is $C_5$–$C_{12}$cycloalkyl, $C_5$–$C_{12}$cycloalkyl which is interrupted by at least one O or N atom, a polycyclic alkyl radical or a polycyclic alkyl radical which is interrupted by at least one O or N atom;

$R_2$ and $R_3$ are independently $C_1$–$C_{18}$alkyl, benzyl, $C_5$–$C_{12}$cycloalkyl or phenyl, which are unsubstituted or substituted by halogen, OH, $COOR_{21}$ or $C(O)$—$R_{22}$ or together with the carbon atom form a $C_5$–$C_{12}$cycloalkyl ring;

if Y is O, $R_4$ and $R_{12}$ are OH, O(alkali-metal) $C_1$–$C_{18}$alkoxy, benzyloxy, $NR_{23}R_{24}$, wherein $R_{23}$ and $R_{24}$ are independently from each other hydrogen, $C_1$–$C_{18}$alkyl or phenyl, which are unsubstituted or substituted by halogen, OH, $COOR_{21}$ or $C(O)$—$R_{22}$;

if Y is $CH_2$, $R_4$ is OH, $C_1$–$C_{18}$alkoxy, benzyloxy, O—C(O)—($C_1$–$C_{18}$)alkyl or $NR_{23}R_{24}$;

$R_{12}$ is a group $C(O)R_{25}$, wherein $R_{25}$ is OH, $C_1$–$C_{18}$alkoxy, benzyloxy, $NR_{23}R_{24}$, wherein $R_{23}$ and $R_{24}$ are independently from each other hydrogen, $C_1$–$C_{18}$alkyl or phenyl, which are unsubstituted or substituted by halogen, OH, $COOR_{21}$ or $C(O)$—$R_{22}$;

$R_5$, $R_6$, $R_7$ and $R_8$ are independently of each other $C_1$–$C_{18}$alkyl, $C_5$–$C_{12}$cycloalykyl or phenyl, with the proviso that not more than two are phenyl; or $R_5$ and $R_6$ and/or $R_7$ and $R_8$ together with the carbon atom form a $C_5$–$C_{12}$cycloalkyl ring;

$R_9$ and $R_{10}$ are independently from each other hydrogen, formyl, $C_2$–$C_{18}$alkylcarbonyl, benzoyl, $C_1$–$C_{18}$alkyl, $C_5$–$C_{12}$cycloalkyl, $C_5$–$C_{12}$cycloalkyl which is interrupted by at least one O or N atom, benzyl or phenyl which are unsubstituted or substituted by halogen, OH, $COOR_{21}$ or $C(O)$—$R_{22}$;

$R_{11}$ is formyl, $C_2$–$C_{18}$alkylcarbonyl, benzoyl, $C_1$–$C_{18}$alkyl, $C_5$–$C_{12}$cycloalkyl, $C_5$–$C_{12}$cycloalkyl which is interrupted by at least one O or N atom, benzyl or phenyl which are unsubstituted or substituted by halogen, OH, $COOR_{21}$ or $C(O)$—$R_{22}$; and X represents a group having at least one carbon atom and is such that the free radical X. derived from X is capable of initiating polymerization of ethylenically unsaturated monomers.

Halogen is Fluorine, Chlorine, Bromine or Iodine, preferably Chlorine or Bromine.

The alkyl radicals in the various substituents may be linear or branched. Examples of alkyl containing 1 to 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl. $C_5$–$C_{12}$cycloalkyl is typically, cyclopentyl, methylcyclopentyl, dimethylcyclopentyl, cyclohexyl, methylcyclohexyl.

Cycloalkyl which is interrupted by at least one O or N atom is for example 2-tetrahydropyran-yl, tetrahydrofurane-yl, 1,4 dioxan-yl, pyrrolidin-yl, tetrahydrothiophen-yl, pyrazolidin-yl, imidazolidin-yl, butyrolactone-yl, caprolactame-yl Examples for alkali metal are lithium, sodium or potassium.

$C_1$–$C_{18}$ alkoxy is for example methoxy, ethoxy, propoxy, butoxy, pentoxy, octoxy, dodecyloxy or octadecyloxy.

$C_2$–$C_{18}$ alkylcarbonyl is for example acetyl, propionyl, butyryl, pentylcarbonyl, hexylcarbonyl or dodecylcarbonyl.

Polycyclic alkyl radicals which may also be interrupted by at least one oxygen or nitrogen atom are for example adamantane, cubane, twistane, norbornane, bypyclo[2.2.2] octane bycyclo[3.2.1]octane, hexamethylentetramine (urotropine) or a group

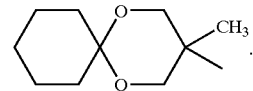

Preferably X is selected from the group consisting of —$CH_2$-aryl,

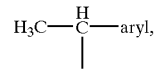

—$CH_2$—$CH_2$-aryl,

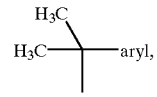

($C_5$–$C_6$cycloalkyl)$_2$CCN, ($C_1$–$C_{12}$alkyl)$_2$CCN, —$CH_2CH$=$CH_2$, ($C_1$–$C_{12}$)alkyl-$CR_{30}$—C(O)—($C_1$–$C_{12}$) alkyl, ($C_1$–$C_{12}$)alkyl-$CR_{30}$—C(O)—($C_6$–$C_{10}$)aryl, ($C_1$–$C_{12}$) alkyl-$CR_{30}$—C(O)—($C_1$–$C_{12}$)alkoxy, ($C_1$–$C_{12}$)alkyl-$CR_{30}$—C(O)-phenoxy, ($C_1$–$C_{12}$)alkyl-$CR_{30}$—C(O)—N-di ($C_1$–$C_{12}$)alkyl, ($C_1$–$C_{12}$)alkyl-$CR_{30}$—CO—NH($C_1$–$C_{12}$) alkyl, ($C_1$–$C_{12}$)alkyl-$CR_{30}$—CO—$NH_2$, —$CH_2CH$=$CH$—$CH_3$, —$CH_2$—$C(CH_3)$=$CH_2$, —$CH_2$—$CH$=$CH$-phenyl, $$—CH_2—C\equiv CH,$$

$(C_1–C_{12})alkyl-CR_{30}—CN,$

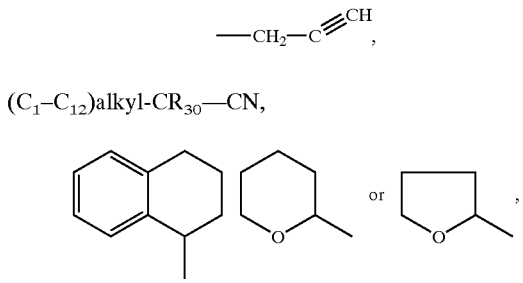

wherein $R_{30}$ is hydrogen or $C_1–C_{12}$alkyl;

the aryl groups are phenyl or naphthyl, which are unsubstituted or substituted with $C_1–C_{12}$alkyl, halogen, $C_1–C_{12}$alkoxy, formyl, $C_2–C_{12}$alkylcarbonyl, glycidyloxy, OH, —COOH or —COOC$_1$–C$_{12}$alkyl.

More preferably X is selected from the group consisting of —CH$_2$-phenyl, CH$_3$CH-phenyl, (CH$_3$)$_2$C-phenyl, (C$_5$–C$_6$cycloalkyl)$_2$CCN, (CH$_3$)$_2$CCN, —CH$_2$CH=CH$_2$, CH$_3$CH—CH=CH$_2$(C$_1$–C$_8$alkyl)CR$_{30}$—C(O)-phenyl, (C$_1$–C$_8$)alkyl-CR$_{30}$—C(O)—(C$_1$–C$_8$)alkoxy, (C$_1$–C$_8$)alkyl-CR$_{30}$—C(O)—(C$_1$–C$_8$)alkyl, (C$_1$–C$_8$)alkyl-CR$_{30}$—C(O)—N-di(C$_1$–C$_8$)alkyl, (C$_1$–C$_8$)alkyl-CR$_{30}$—C(O)—NH(C$_1$–C$_8$)alkyl, (C$_1$–C$_8$)alkyl-CR$_{30}$—C(O)—NH$_2$, (C$_1$–C$_{12}$)alkyl-CR$_{30}$—CN, wherein R$_{30}$ is hydrogen or (C$_1$–C$_8$)alkyl.

Most preferably X is selected from the group consisting of —CH$_2$-phenyl, CH$_3$CH-phenyl, (CH$_3$)$_2$C-phenyl, (C$_5$–C$_6$cycloalkyl)$_2$CCN, (CH$_3$)$_2$CCN, —CH$_2$CH=CH$_2$, CH$_3$CH—CH=CH$_2$(C$_1$–C$_4$alkyl)CR$_{30}$—C(O)-phenyl, (C$_1$–C$_4$)alkyl-CR$_{30}$—C(O)—(C$_1$–C$_4$)alkoxy, (C$_1$–C$_4$)alkyl-CR$_{30}$—C(O)—(C$_1$–C$_4$)alkyl, (C$_1$–C$_4$)alkyl-CR$_{30}$—C(O)—N-di(C$_1$–C$_4$)alkyl, (C$_1$–C$_4$)alkyl-CR$_{30}$—C(O)—NH (C$_1$–C$_4$)alkyl-CR$_{30}$—C(O)—NH$_2$, wherein R$_{30}$ is hydrogen or (C$_1$–C$_4$)alkyl.

Preferred compounds are those, wherein

Y and Q are O.

A preferred subgroup of compounds are those of formula (Ia), wherein Y is Q;

$R_1$ is tertiary $C_4–C_{18}$alkyl, $C_5–C_{12}$cycloalkyl, $C_5–C_{12}$cycloalkyl which is interrupted by at least one O or N atom or a polycyclic alkyl radical;

$R_2$ and $R_3$ are independently $C_1–C_{10}$alkyl, benzyl, phenyl, which are unsubstituted or substituted by halogen, OH, COOR$_{21}$ or C(O)—R$_{22}$ or together with the carbon atom form a $C_5–C_{12}$cycloalkyl ring;

$R_4$ is $C_1–C_{18}$alkoxy, benzyloxy or NR$_{23}$R$_{24}$, wherein $R_{23}$ and $R_{24}$ are independently of each other hydrogen or $C_1–C_{18}$alkyl.

Amongst this subgroup those compounds of formula (Ia) are particularly preferred, wherein $R_1$ is tertiary $C_4–C_8$alkyl;

$R_2$ and $R_3$ are methyl, ethyl or together with the carbon atom form a $C_5–C_6$cycloalkyl ring;

$R_4$ is $C_1–C_{18}$alkoxy, benzyloxy or NR$_{23}$R$_{24}$, wherein $R_{23}$ and $R_{24}$ are independently of each other hydrogen or $C_1–C_8$alkyl.

The definition and preferences for X apply also for the subgroups according to formula (Ia).

Another preferred subgroup of compounds are those of formula (Ib), wherein Q is O;

$R_5$, $R_6$, $R_7$ and $R_8$ are independently of each other $C_1–C_{10}$alkyl, $C_5–C_{12}$cycloalkyl; or $R_5$ and $R_6$ and/or $R_7$ and $R_8$ together with the carbon atom form a $C_5–C_{12}$cycloalkyl ring;

$R_9$ and $R_{10}$ are independently of each other formyl, $C_2–C_{18}$alkylcarbonyl, benzoyl, $C_1–C_{18}$alkyl, benzyl or phenyl.

Within the subgroup of compounds of formula (Ib) those are particularly preferred, wherein Q is O;

$R_5$, $R_6$, $R_7$ and $R_8$ are independently of each other methyl, ethyl; or $R_5$ and $R_6$ and/or $R_7$ and $R_8$ together with the carbon atom form a $C_5–C_6$cycloalkyl ring;

$R_9$ and $R_{10}$ are independently of each other formyl, $C_2–C_8$alkylcarbonyl, benzoyl, $C_1–C_8$alkyl, benzyl or phenyl.

The definition and preferences for X apply also for the subgroups according to formula (Ib).

Still another preferred subgroup of compounds are those of formula (Ic), wherein Y is O $R_5$, $R_6$, $R_7$ and $R_8$ are independently of each other $C_1–C_{10}$alkyl, $C_5–C_{12}$cycloalkyl; or $R_5$ and $R_6$ and/or $R_7$ and $R_8$ together with the carbon atom form a $C_5–C_{12}$cycloalkyl ring;

$R_{11}$ is formyl, $C_2–C_{18}$alkylcarbonyl, benzoyl, $C_1–C_{18}$alkyl, benzyl or phenyl and $R_{12}$ is OH, $C_1–C_{18}$alkoxy, benzyloxy, NR$_{23}$R$_{24}$, wherein $R_{23}$ and $R_{24}$ are independently of each other hydrogen, $C_1–C_{18}$alkyl or phenyl.

Within the subgroup of compounds of formula (Ic) those are particularly preferred, wherein Y is O $R_5$, $R_6$, $R_7$ and $R_8$ are independently of each other methyl, ethyl; or $R_5$ and $R_6$ and/or $R_7$ and $R_8$ together with the carbon atom form a $C_5–C_6$cycloalkyl ring;

$R_{11}$ is formyl, $C_2–C_{18}$alkylcarbonyl, benzoyl, $C_1–C_{18}$alkyl, benzyl or phenyl and $R_{12}$ is OH, $C_1–C_{18}$alkoxy, benzyloxy, NR$_{23}$R$_{24}$, wherein $R_{23}$ and $R_{24}$ are independently of each other hydrogen or $C_1–C_{18}$alkyl.

Another object of the present invention is a polymerizable composition, comprising a) at least one ethylenically unsaturated monomer or oligomer, and b) at least one compound of formula (Ia), (Ib) or (Ic).

Typically the ethylenically unsaturated monomer or oligomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl) acrylic acidanhydrides, (alkyl)acrylic acid salts, (alkyl) acrylic esters, (meth)acrylo-nitriles, (alkyl)acrylamides, vinyl halides or vinylidene halides.

Preferred ethylenically unsaturated monomers are ethylene, propylene, n-butylene, i-butylene, isoprene, 1,3-butadiene, α-C$_5$–C$_{18}$alkene, styrene, α-methyl styrene, p-methyl styrene or a compound of formula CH$_2$=C(R$_a$)—(C=Z)—R$_b$, wherein R$_a$ is hydrogen or C$_1$–C$_4$alkyl, R$_b$ is NH$_2$, O$^-$(Me$_+$), glycidyl, unsubstituted C$_1$–C$_{18}$alkoxy, C$_2$–C$_{100}$alkoxy interrupted by at least one N and/or O atom, or hydroxy-substituted C$_1$–C$_{18}$alkoxy, unsubstituted C$_1$–C$_{18}$alkylamino, di(C$_1$–C$_{18}$alkyl)amino, hydroxy-substituted C$_1$–C$_{18}$alkylamino or hydroxy-substituted di(C$_1$–C$_{18}$alkyl)amino, —O—CH$_2$—CH$_2$—N(CH$_3$)$_2$ or —O—CH$_2$—CH$_2$—N$^+$H(CH$_3$)$_2$ An$^-$;

An⁻ is a anion of a monovalent organic or inorganic acid;

Me is a monovalent metal atom or the ammonium ion.

Z is oxygen or sulfur.

Examples for $R_a$ as $C_2$–$C_{100}$alkoxy interrupted by at least one O atom are of formula

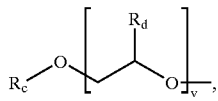

wherein $R_c$ is $C_1$–$C_{25}$alkyl, phenyl or phenyl substituted by $C_1$–$C_{18}$alkyl, $R_d$ is hydrogen or methyl and v is a number from 1 to 50. These monomers are for example derived from non ionic surfactants by acrylation of the corresponding alkoxylated alcohols or phenols. The repeating units may be derived from ethylene oxide, propylene oxide or mixtures of both.

Further examples of suitable acrylate or methacrylate monomers are given below.

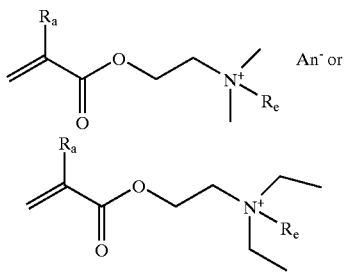

An⁻, wherein An⁻ and $R_a$ have the meaning as defined above and $R_e$ is methyl or benzyl. An⁻ is preferably Cl⁻, Br⁻ or ⁻$O_3$S—$CH_3$.

Further acrylate monomers are

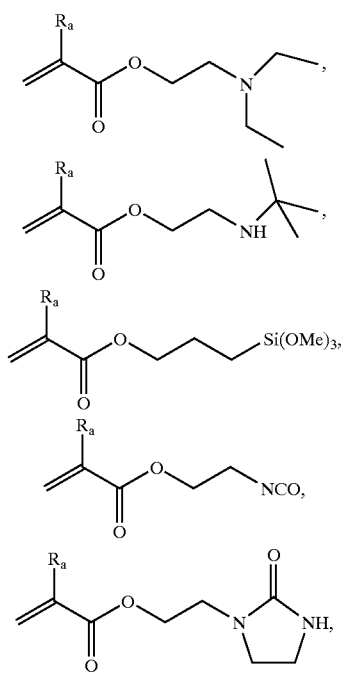

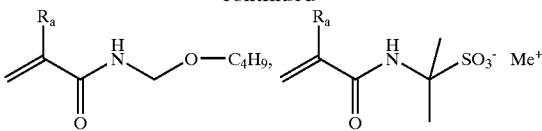

Examples for suitable monomers other than acrylates are

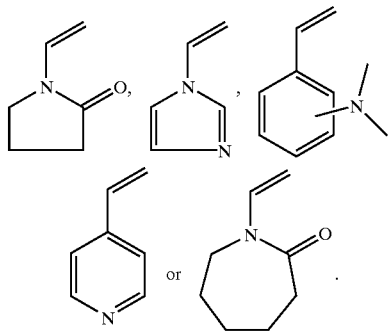

Preferably $R_a$ is hydrogen or methyl, $R_b$ is $NH_2$, gycidyl, unsubstituted or with hydroxy substituted $C_1$–$C_4$alkoxy, unsubstituted $C_1$–$C_4$alkylamino, di($C_1$–$C_4$alkyl)amino, hydroxy-substituted $C_1$–$C_4$alkylamino or hydroxy-substituted di($C_1$–$C_4$alkyl)amino; and Z is oxygen.

Particularly preferred ethylenically unsaturated monomers are styrene, methylacrylate, ethylacrylate, butylacrylate, isobutylacrylate, tert. butylacrylate, hydroxyethylacrylate, hydroxypropylacrylate, dimethylaminoethylacrylate, glycidylacrylates, methyl (meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth) acrylates, acrylonitrile, acrylamide, methacrylamide or dimethylaminopropyl-methacrylamide.

It is also possible to enhance the rate of polymerization or copolymerization of slowly polymerizing monomers such as for example of the class of methacrylates, in particular methylmethacrylate by the addition of more readily polymerizable comonomers such as acrylates. Typical examples are the polymerization or copolymerization of methyl-methacrylate in the presence of methylacrylate or butylacrylate.

Typical slowly polymerizing methacrylates are methyl (meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth) acrylates, methacrylamide or dimethylaminopropyl-methacrylamide. The polymerization of these methacrylates can be enhanced by the addition of the corresponding acrylates.

Preferred is a composition, wherein the ethylenically unsaturated monomer is a mixture of a methacrylate and an acrylate.

The amounts of readily polymerizable comonomers range typically from 5 parts to 95 and the slowly polymerizable monomers range from 95 to 5 parts respectively.

The initiator compound is preferably present in an amount of from 0.1 mol-% to 30 mol-%, more preferably in an amount of from 0.1 mol-% to 20 mol-%, and most preferably in an amount of from 0.5 mol-% to 10 mol-% based on the monomer or monomer mixture.

A further object of the present invention is a process for preparing an oligomer, a cooligomer, a polymer or a copolymer (block or random) by free radical polymerization of at least one ethylenically unsaturated monomer or oligomer, which comprises (co)polymerizing the monomer or monomers/oligomers in the presence of at least one initiator compound of formula (Ia), (Ib) or (Ic) under reaction conditions capable of effecting scission of the O—C bond to form two free radicals, the radical .X being capable of initiating polymerization.

Typically the scission of the O—C bond is effected by ultrasonic treatment, heating or exposure to electromagnetic radiation, ranging from γ to microwaves.

Preferably the scission of the O—C bond is effected by heating and takes place at a temperature of between 50° C. and 160° C., more preferably between 80° C. and 150° C.

The process may be carried out in the presence of an organic solvent or in the presence of water or in mixtures of organic solvents and water. Additional cosolvents or surfactants, such as glycols or ammonium salts of fatty acids, may be present. Other suitable cosolvents are described hereinafter.

Preferred processes use as little solvents as possible. In the reaction mixture it is preferred to use more than 30% by weight of monomer and initiator, particularly preferably more than 50% and most preferrably more than 80%. In many cases it is possible to polymerize without any solvent.

If organic solvents are used, suitable solvents or mixtures of solvents are typically pure alkanes (hexane, heptane, octane, isooctane), hydrocarbons (benzene, toluene, xylene), halogenated hydrocarbons (chlorobenzene), alkanols (methanol, ethanol, ethylene glycol, ethylene glycol monomethyl ether), esters (ethyl acetate, propyl, butyl or hexyl acetate) and ethers (diethyl ether, dibutyl ether, ethylene glycol dimethyl ether), or mixtures thereof.

The aqueous polymerization reactions can be supplemented with a water-miscible or hydrophilic cosolvent to help ensure that the reaction mixture remains a homogeneous single phase throughout the monomer conversion. Any water-soluble or water-miscible cosolvent may be used, as long as the aqueous solvent medium is effective in providing a solvent system which prevents precipitation or phase separation of the reactants or polymer products until after all polymerization reactions have been completed. Exemplary cosolvents useful in the present invention may be selected from the group consisting of aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosulfides, sulfoxides, sulfones, alcohol derivatives, hydroxyether derivatives such as butyl carbitol or cellosolve, amino alcohols, ketones, and the like, as well as derivatives thereof and mixtures thereof. Specific examples include methanol, ethanol, propanol, dioxane, ethylene glycol, propylene glycol, diethylene glycol, glycerol, dipropylene glycol, tetrahydrofuran, and other water-soluble or water-miscible materials, and mixtures thereof. When mixtures of water and water-soluble or water-miscible organic liquids are selected as the aqueous reaction media, the water to cosolvent weight ratio is typically in the range of about 100:0 to about 10:90.

The process is particularly useful for the preparation of block copolymers.

Block copolymers are, for example, block copolymers of polystyrene and polyacrylate (e.g., poly(styrene-co-acrylate) or poly(styrene-co-acrylate-co-styrene). They are useful as adhesives or as compatibilizers for polymer blends or as polymer toughening agents. Poly(methylmethacrylate-co-acrylate) diblock copolymers or poly(methylacrylate-co-acrylate-co-methacrylate) triblock copolymers) are useful as dispersing agents for coating systeme, as coating additives (e.g. rheological agents, compatibilizers, reactive diluents) or as resin component in coatings(e.g. high solid paints) Block copolymers of styrene, (meth)acrylates and/or acrylonitrile are useful for plastics, elastomers and adhesives.

Furthermore, block copolymers of this invention, wherein the blocks alternate between polar monomers and non-polar monomers, are useful in many applications as amphiphilic surfactants or dispersants for preparing highly uniform polymer blends.

The (co)polymers of the present invention may have a number average molecular weight from 1 000 to 400 000 g/mol, preferably from 2 000 to 250 000 g/mol and, more preferably, from 2 000 to 200 000 g/mol. The number average molecular weight may be determined by size exclusion chromatography (SEC), gel permeation chromatography (GPC), matrix assisted laser desorption/ionization mass spectrometry (MALDI-MS) or, if the initiator carries a group which can be easily distinguished from the monomer (s), by NMR spectroscopy or other conventional methods.

The polymers or copolymers of the present invention have preferably a polydispersity of from 1.1 to 2, more preferably of from 1.2 to 1.8.

Thus, the present invention also encompasses in the synthesis novel block, multi-block, star, gradient, random, hyperbranched and dendritic copolymers, as well as graft copolymers.

The definitions and preferences for the different substituents given for the compounds, apply also for the composition and for the polymerization process. The polymers prepared by the present invention are useful for following applications: adhesives, detergents, dispersants, emulsifiers, surfactants, defoamers, adhesion promoters, corrosion inhibitors, viscosity improvers, lubricants, rheology modifiers, thickeners, crosslinkers, paper treatment, water treatment, electronic materials, paints, coatings, photography, ink materials, imaging materials, superabsorbants, cosmetics, hair products, preservatives, biocide materials or modifiers for asphalt, leather, textiles, ceramics and wood.

Because the present polymerizaton is a "living" polymerization, it can be started and stopped practically at will. Furthermore, the polymer product retains the functional alkoxyamine group allowing a continuation of the polymerization in a living matter. Thus, in one embodiment of this invention, once the first monomer is consumed in the initial polymerizing step a second monomer can then be added to form a second block on the growing polymer chain in a second polymerization step. Therefore it is possible to carry out additional polymerizations with the same or different monomer(s) to prepare multi-block copolymers.

Furthermore, since this is a radical polymerization, blocks can be prepared in essentially any order. One is not necessarily restricted to preparing block copolymers where the sequential polymerizing steps must flow from the least stabilized polymer intermediate to the most stabilized polymer intermediate, such as is the case in ionic polymerization. Thus it is possible to prepare a multi-block copolymer in which a polyacrylonitrile or a poly(meth)acrylate block is prepared first, then a styrene or butadiene block is attached thereto, and so on.

Furthermore, there is no linking group required for joining the different blocks of the present block copolymer. One can simply add successive monomers to form successive blocks.

A plurality of specifically designed polymers and copolymers are accessible by the present invention, such as star and graft (co)polymers as described, inter alia, by C. J. Hawker in Angew. Chemie, 1995, 107, pages 1623–1627, dendrimers as described by K. Matyaszewski et al. in Macrmolecules 1996, Vol 29, No. 12, pages 4167–4171, graft (co)polymers as described by C. J. Hawker et al. in Macromol. Chem. Phys. 198, 155–166(1997), random copolymers as described by C. J. Hawker in Macromolecules 1996, 29, 2686–2688, or diblock and triblock copolymers as described by N. A. Listigovers in Macromolecules 1996, 29, 8992–8993.

Still another object of the present invention is a compound according to formula IIa, IIb or IIc

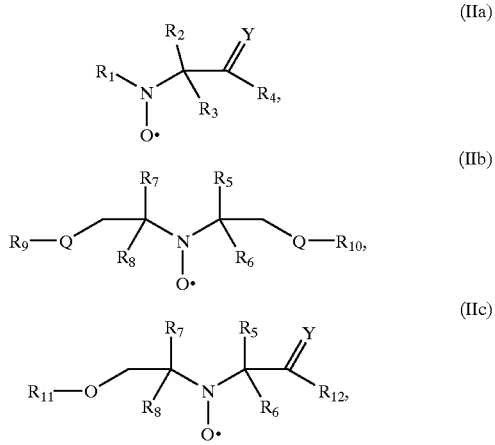

wherein

Y is O or $CH_2$;

Q is O or $NR_{20}$, wherein $R_{20}$, is hydrogen or $C_1$–$C_{18}$alkyl;

$R_1$ is tertiary $C_4$–$C_{18}$alkyl or phenyl, which are unsubstituted or substituted by halogen, OH, $COOR_{21}$ or $C(O)$—$R_{22}$ wherein $R_{21}$ is hydrogen, a alkali metal atom or $C_1$–$C_{18}$alkyl and $R_{22}$ is $C_1$–$C_{18}$alkyl; or $R_1$ is $C_5$–$C_{12}$cycloalkyl, $C_5$–$C_{12}$cycloalkyl which is interrupted by at least one O or N atom, a polycyclic alkyl radical or a polycyclic alkyl radical which is interrupted by at least one O or N atom;

$R_2$ and $R_3$ are independently $C_1$–$C_{18}$alkyl, benzyl, $C_5$–$C_{12}$cycloalkyl, phenyl, which are unsubstituted or substituted by halogen, OH, $COOR_{21}$ or $C(O)$—$R_{22}$ or together with the carbon atom form a $C_5$–$C_{12}$cycloalkyl ring;

if Y is O, $R_4$ and $R_{12}$ are OH, O(alkali-metal) $C_1$–$C_{18}$alkoxy, benzyloxy, $NR_{23}R_{24}$, wherein $R_{23}$ and $R_{24}$ are independently from each other hydrogen, $C_1$–$C_{18}$alkyl or phenyl, which are unsubsbtuted or substituted by halogen, OH, $COOR_{21}$ or $C(O)$—$R_{22}$;

if Y is $CH_2$, $R_4$ is OH, $C_1$–$C_{18}$alkoxy, benzyloxy, O—C(O)—($C_1$–$C_{18}$)alkyl or $NR_{23}R_{24}$;

$R_{12}$ are a group $C(O)R_{25}$, wherein $R_{25}$ is OH, $C_1$–$C_{18}$alkoxy, benzyloxy, $NR_{23}R_{24}$, wherein $R_{23}$ and $R_{24}$ are independently from each other hydrogen, $C_1$–$C_{18}$alkyl or phenyl, which are unsubstituted or substituted by halogen, OH, $COOR_{21}$ or $C(O)$—$R_{22}$;

$R_5$, $R_6$, $R_7$ and $R_8$ are independently of each other $C_1$–$C_{18}$alkyl, $C_5$–$C_{12}$cycloalykyl or phenyl, with the proviso that not more than two are phenyl; or $R_5$ and $R_6$ and/or $R_7$ and $R_8$ together with the carbon atom form a $C_5$–$C_{12}$cycloalkyl ring;

$R_9$ and $R_{10}$ are independently of each other hydrogen, formyl, $C_2$–$C_{18}$alkylcarbonyl, benzoyl, $C_1$–$C_{18}$alkyl, $C_5$–$C_{12}$cycloalkyl, $C_5$–$C_{12}$cycloalkyl which is interrupted by at least one O or N atom, benzyl or phenyl which are unsubstituted or substituted by halogen, OH, $COOR_{21}$, or $C(O)$—$R_{22}$; and $R_{11}$, is formyl, $C_2$–$C_{18}$alkylcarbonyl, benzoyl, $C_1$–$C_{18}$alkyl, $C_5$–$C_{12}$cycloalkyl, $C_5$–$C_{12}$cycloalkyl which is interrupted by at least one O or N atom, benzyl or phenyl which are unsubstituted or substituted by halogen, OH, $COOR_{21}$ or $C(O)$—$R_{22}$.

These compounds are intermediates of the title compounds and may also be used together with a radical source to effect polymerization of ethylenically unsaturated monomers or oligomers.

Consequently further objects of the invention are a polymerizable composition, comprising a) at least one ethylenically unsaturated monomer or oligomer, and b) at least one compound of formula (IIa), (IIb) or (IIc) and c) a radical iniator X. capable of initiating polymerization of ethylenically unsaturated monomers and a process for preparing an oligomer, a cooligomer, a polymer or a copolymer (block or random) by free radical polymerization, which comprises subjecting above composition to heat or actinic radiation.

It is also possible and in some cases it may be advantageous to effect polymerization in the presence of a mixture of compounds of formula Ia, Ib, Ic and IIa, IIb, IIc. Typically the nitroxides of formula IIa, b, c are present in an amount of 0.1 to 10% by weight, based on the amount nitroxide ethers of formula Ia, b, c.

Preferably the nitroxides of formula IIa, b, c are present in an amount of 1 to 5% by weight, based on the amount nitroxide ethers of formula Ia, b, c.

Consequently another object of the present invention is a polymerizable composition comprising a) at least one ethylenically unsaturated monomer or oligomer;

b) at least one compound of formula (Ia), (Ib) or (Ic) and c) at least one compound of formula (IIa), (IIb) or (IIc).

The production of C-centered radicals X. is described, inter alia, in Houben Weyl, Methoden der Organischen Chemie, Vol. E 19a, pages 60–147. These methods can be applied in general analogy.

The source of radicals X. may be a bis-azo compound, a peroxide or a hydroperoxide.

Most preferably, the source of radicals X. is 2,2'-azobisisobutyronitrile, 2,2'-azobis(2-methylbutyronitrile), 2,2'-azobis(2,4-dimethylvaleronitrile), 2,2'-azobis(4-methoxy-2,4dimethylvaleronitrile), 1,1 '-azobis(1-cyclohexanecarbonitrile), 2,2'-azobis(isobutyramide) dihydrate, 2-phenylazo-2,4-dimethyl-4-methoxyvaleronitrile, dimethyl-2,2'-azobisisobutyrate, 2-carabamoylazo)isobutyronitrile, 2,2'-azobis(2,4,4-trimethylpentane), 2,2'-azobis(2-methylpropane), 2,2'-azobis(N,N'-dimethyleneisobutyramidine), free base or hydrochloride, 2,2'-azobis(2-amidinopropane), free base or hydrochloride, 2,2'-azobis{2-methyl-N-[1,1-bis(hydroxymethyl)ethyl]propionamide} 2,2'-azobis{2-methyl-N-[1,1-bis(hydroxymethyl)-2-hydroxyethyl] propionamide.

Preferred peroxides and hydroperoxides are acetyl cyclohexane sulphonyl peroxide, diisopropyl peroxy dicarbonate, t-amyl perneodecanoate, t-butyl perneodecanoate, t-butyl perpivalate, t-amylperpivalate, bis(2,4-dichlorobenzoyl) peroxide, diisononanoyl peroxide, didecanoyl peroxide, dioctanoyl peroxide, dilauroyl peroxide, bis(2-methylbenzoyl) peroxide, disuccinic acid peroxide, diacetyl peroxide, dibenzoyl peroxide, t-butyl per 2-ethylhexanoate, bis-(4-chlorobenzoyl)-peroxide, t-butyl perisobutyrate, t-butyl permaleinate, 1,1-bis(t-butylperoxy)3,5,5-trimethylcyclohexane, 1,1-bis(t-butylperoxy)cyclohexane, t-butyl peroxy isopropyl carbonate, t-butyl perisononaoate, 2,5-dimethylhexane 2,5-dibenzoate, t-butyl peracetate, t-amyl perbenzoate, t-butyl perbenzoate, 2,2-bis(t-butylperoxy)butane, 2,2 bis(t-butylperoxy)propane, dicumyl peroxide, 2,5-dimethylhexane-2,5-di-t-butylperoxide, 3-t-butylperoxy 3-phenylphthalide, di-t-amyl peroxide, α,α'-bis (t-butylperoxy isopropyl) benzene, 3,5-bis(t-butylperoxy)3, 5-dimethyl 1,2-dioxolane, di-t-butyl peroxide, 2,5-dimethylhexyne-2,5-di-t-butylperoxide, 3,3,6,6,9,9-hexamethyl 1,2,4,5-tetraoxa cyclononane, p-menthane hydroperoxide, pinane hydroperoxide, diisopropylbenzene mono-α-hydroperoxide, cumene hydroperoxide or t-butyl hydroperoxide.

These compounds are commercially available.

If more than one radical source is used, a mixture of substitution patterns is obtainable.

The molar ratio of the radical source to the compound of formulae IIa, IIb or IIc may be from 1:10 to 10:1, preferably from 1:5 to 5:1 and more preferably from 1:2 to 2:1.

The present invention encompasses also a polymer or oligomer having attached at least one initiator group —X and at least one oxyamine group of formula (IIIa), (IIIb) or (IIIc)

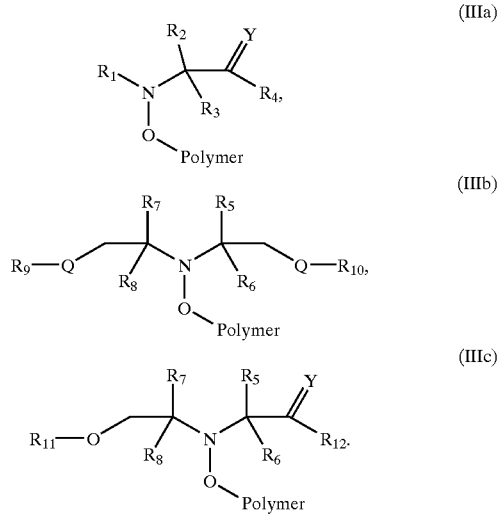

The use of a compound of formula (Ia), (Ib) or (Ic) or of a compound of formula (IIa), (IIb), or (IIc) for the polymerization of ethylenically unsaturated monomers or oligomers is a further object of the present invention.

Definitions and preferences mentioned above for the compounds apply for all objects of the invention.

The compounds of the present invention can be prepared by known methods.

A suitable way to prepare compounds of formula (Ia) is to start from the corresponding amines. The amines, wherein Y is O are known and can be prepared for example by ozonolysis of tert.-alkyl-allylamines according to U.S. Pat. No. 3,203,981

Alternatively reaction of a tertiary amine with $CHCl_3$ and a ketone is also possible. J. T. Lai. in J. Org. Chem. 45, 3671 (1980).

Other possibilities are according to F. S. Guziec, F. F. Torres.: J. Org. Chem. 58, 1604 (1993) or the reaction of an aziridinone with an alcoholate according to H. Quast et. al.: Chem. Ber. 120, 217 (1987).

S. A. Kedik, E. G. Rozantsev, A. A. Usvyatsov.: Doklady Akademii Nauk SSSR, 257 (6), 1382 (1981) have reported on the oxidative cleavage of a 2,2,6,6-tetraalkyl-4-oxopiperidine, which also leads to the corresponding amines.

If Y is $CH_2$ reduction of the corresponding carbonyl compound is possible as described by J. T. Lai.: Tet. Lett., 23, 595 (1982)):

To prepare compounds of formula (Ib) it is also suitable to start from the corresponding amines which are known per se. They can be prepared by reduction of 3,3,5,5-tetra-substituted-2-oxo-morpholinones and subsequent reaction of the alcohol groups (J. T. Lai.: Synthesis, 122 (1984)), or by reduction of the corresponding bis(cyanoalkyl)-amines according to J. V. Dubsky, W. D. Wensink.: Chem. Ber. 49, 1134 (1916).

The amines corresponding to formula (Ic) are accessible in the same manner, starting from the corresponding amines. The amines may be prepared according to S. A. Kedik, E. G. Rozantsev, A. A. Usvyatsov.: Doklady Akademii Nauk SSSR, 257 (6), 1382 (1981) or J. T. Lai.: Synthesis, 122 (1984).

The functional groups may be further reacted according to standard methods to obtain ethers or esters.

A further possibility is ring opening of 3,3,5,5-tetrasubstituted-2-oxo-morpholinones with primary or secondary amines. The resulting amides may be further functionalized.

The Oxidation of the amines to Nitroxides is well known and for example described in L. B. Volodarsky, V. A. Reznikov, V. I. Ovcharenko.: Synthetic Chemistry of Stable Nitroxides, CRC Press, Boca Raton 1994.

The NOR compounds are prepared for example by reacting the Nitroxides with free radicals. The radicals may be generated by scission of peroxy- or azo compounds as for example described by T. J. Connolly, M. V. Baldovi, N. Mohtat, J. C. Scaiano.: Tet. Lett. 37, 4919 (1996) or by I. Li, B. A. Howell et al.: Polym. Prepr. 36, 469 (1996).

Another possibility is a halogen atom transfer from a alkylhalogenide in the presence of Cu(I) as described by K. Matyjaszewski.: Macromol. Symp. 111, 47–61 (1996).) or a one electron oxidation as described by P. Stipa, L. Greci, P. Carloni, E. Damiani.: Polym. Deg. Stab. 55, 323 (1997))

Further possibilities are the O-alkylation of the corresponding hydroxylamine, as for example described by Said Oulad Hammouch, J. M. Catala.: Macromol. Rapid Commun. 17, 149–154 (1996), Meisenheinmer rearrangement of the corresponding N-Allyl-N-oxids as described by B. Walchuk et al.: Polymer Preprints 39, 296 (1998) or the reaction of a oxoammonium salt with a carbonyl compound, as described by Tan Ren, You-Cheng Liu, Qing-Xiang Guo.: Bull. Chem. Soc. Jpn. 69, 2935 (1996).

The following examples illustrate the invention.

A) PREPARATION OF COMPOUNDS

In Table 1 the nitroxide intermediates prepared are summarized.

TABLE 1

| No. | Structure |
|---|---|
| 101 | 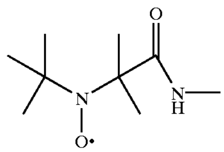 |
| 102 | 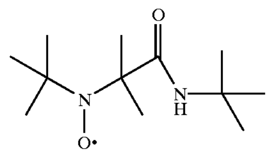 |
| 103 | 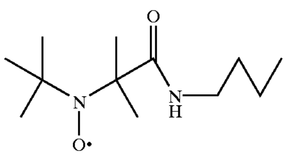 |
| 104 | 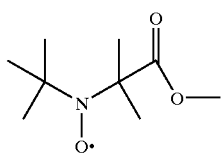 |
| 105 | 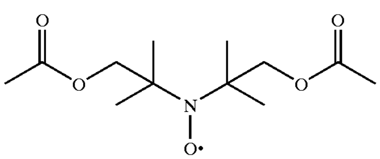 |
| 106 | 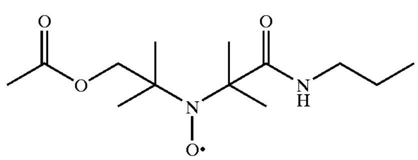 |
| 107 | 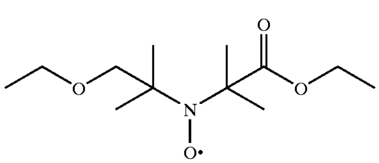 |
| 108 | 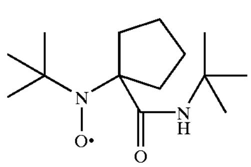 |
| 109 | 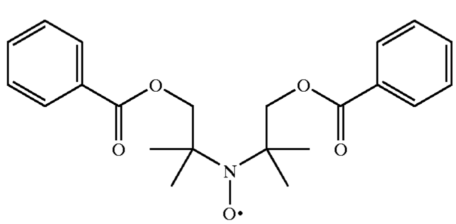 |

EXAMPLE A1

Preparation of tert-butyl-(dimethyl-methylaminocarbonyl-methyl)-amine-N-oxyl (101)

To a solution of 21.15 g (0.122 mol) tert-butyl-(dimethyl-methylaminocarbonyl-methyl)-amine (prepared according to F. S. Guziec, F. F. Torres.: J. Org. Chem. 58, 1604 (1993)) in 70 ml methanol 2 g sodium carbonate, 2 g sodiumwolframate and 70 ml $H_2O_2$ 30% are added at 20° C. The solution is stirred for 17 h at 20° C. 20 g solid NaCl are added and the red mixture is extracted with toluene-ethylacetate. The extracts are combined, washed with saturated NaCl solution, dried over $MgSO_4$ and concentrated under vacuum. The residue is purified by chromatography on silica gel (hexane-ethylacetate 1:1). 14.6 g (64%) of the title nitroxide are obtained with a m.p. of 84–90° C.

Elemental analysis calculated for $C_9H_{19}N_2O_2$: C 57.73%; H 10.23%; N 14.96%. Found: C 57.49%; H 10.15%; N 14.90%.

EXAMPLE A2

Preparation of tert-butyl-(dimethyl-tert-butylaminocarbonyl-methyl)-amine-N-oxyl (102)

To a solution of 32.15 g (0.15 mol) tert-butyl-tert-butylaminocarbonyl-methyl)-amine (prepared according to F. S. Guziec, F. F. Torres.: J. Org. Chem. 58, 1604 (1993)) in 50 ml methanol 2 g sodium carbonate, 0.5 g sodium wolframate are added. 58.3 g $H_2O_2$ 35% are added at 20° C. The solution is stirred for 22 h at 20° C. 10 g solid NaCl are added and the red mixture is extracted with hexane. The extracts are combined, washed with saturated NaCl solution, dried over $MgSO_4$ and concentrated under vacuum. The residue is purified by recrystallization from pentane. 26.05 g (75%) of the title nitroxide are obtained with a m.p. of 46–49° C.

Elemental analysis calculated for $C_{12}H_{25}N_2O_2$: C 62.84%; H 10.99%; N 12.21%. Found: C 63.10%; H 10.28%; N 12.37%.

EXAMPLE A3

Preparation of tetra-butyl-(dimethyl-n-butylaminocarbonyl-methyl)-amine-N-oxyl (103)

Preparation of tert-butyl-(dimethyl-n-butylaminocarbonyl-methyl)-amine

The compound is prepared in analogy to P. Scrimin et al: Synthesis 1092 (1982). A colorless oil is obtained.

$^1$H-NMR (CDCl$_3$), δ (ppm): 7.52 m (NH), 3.20 q (2H), 1.45 m (2H), 1.36 s (6H), 1.14 s (9H), 0.93 t (3H).

To a solution of 6.75 g sodium carbonate, 1 g sodium wolframate and 41 ml $H_2O_2$ 30% at 20° C. a solution of 12.9 g (0.06 mol) tert-butyl-(dimethyl-n-butylaminocarbonyl-methyl)-amine in 70 ml methanol are dropwise added. After stirring for 17 h at 20° C.,—20 g NaCl are added and the red mixture is extracted with toluene-methyl-tert-butylether. The combined extracts are washed with saturated NaCl solution, dried over $MgSO_4$ and concentrated under vacuum. The residue is purified by chromatography on silica gel (hexane-ethylacetate 4:1). 7.3 g (53%) of the title nitroxide are obtained as red slowly solidifying oil.

Elemental analysis calculated for $C_{12}H_{25}N_2O_2$: C 62.84%; H 10.99%; N 12.21%. Found: C 62.55%; H 10.93%; N 12.29%.

EXAMPLE A4

Preparation of tert-butyl-(dimethyl-methoxycarbonyl-methyl)-amine-N-oxyl (104)

To a solution of 4.35 g (0.025 mol) tert-butyl-(dimethyl-methoxycarbonyl-methyl)-amine (prepared according to H. Quast et al.: Chem. Ber. 120, 217 (1987)) in 50 ml ethylacetate a solution of 10 g m-chlorperbenzoic acid (0.04 mol) in 20 ml ethylacetate is dropwise added at 10° C. The mixture is stirred for 4 h at room temperature and extracted severeal times with aNaHCO$_3$ solution. The organic phase is dried over MgSO$_4$ and concentrated under vacuum. The residue is purified by chromatography over silica gel (hexane-ethylacetate 9:1). 2.6 g (55%) of the title compound are obtained as red oil.

Elemental analysis calculated for C$_9$H$_{18}$NO$_3$: C 57.42%; H 9.64%; N 7.44%. Found: C 57.68%; H 9.60%; N 7.35%.

EXAMPLE A5

Preparation of bis-(dimethyl-acetoxymethyl-methyl)-amine-N-oxyl (105)

Preparation of bis-(dimethyl-acetoxymethyl-methyl)-amine 7.7 g (0.048 mol) bis-(dimethyl-hydroxymethyl-methyl)-amine (prepared according to L. T. Lai.: Synthesis 122 (1984)) are dissolved in 80 ml dichlormethane and 6.95 ml (0.098 mol) acetylchloride are added. The mixture is stirred for 12 h at room temperature and washed with a NaHCO$_3$ solution. The organic phase is dried over MgSO$_4$ and concentrated under vacuum. The residue is purified by chromatography over silica gel (ethylacetate ) 10.3 g (88%) of the title compound are obtained as colorless oil.

$^1$H-NMR (CDCl$_3$), δ (ppm): 3.88 s (4H), 2.08 s (6H), 1.18 s (12 H).

To a solution of 9.0 g (0.037 mol) bis-(dimethyl-acetoxymethyl-methyl)-amine in 40 ml ethylacetate at 10° C. a solution of 13.6 g m-Chlorperbenzoic acid (0.055 mol) in 30 ml ethylacetate are dropwise added. The mixture is stirred for 1.5 h at room temperature, washed with a NaHCO$_3$ solution, the organic phase dried over MgSO$_4$ and concentrated under vacuum. The residue is purified by chromatography over silica gel (hexane-ethylacetate 2:1). 8.9 g (82%) of the title compound are obtained as red oil.

Elemental analysis calculated for C$_{12}$H$_{22}$NO$_5$: C 55.37%; H 8.52%; N 5.38%. Found: C 55.27%; H 8.32%; N 5.29%.

EXAMPLE A6

Preparation of (dimethyl-acetoxymethyl-methyl)-(dimethyl-propylamino-carbonyl-methyl)-amino-N-oxyl (106)

Preparation of (dimethyl-acetoxymethyl-methyl)-(dimethyl-propylaminocarbonyl-methyl)-amine 20 g (0.127 mol) 3,3,5,5-Tetramethyl-2-oxo-morpholinon (prepared according to J. T. Lai.: Synthesis, 122 (1984)) are dissolved in 31.5 ml (0.381 mol) n-propylamine and the mixture refluxed for 12 h. After distillation of excess propylamine under vacuum 27 g (98%) (dimeth-hydroxymethyl-methyl)-(dimethyl-propylaminocarbonyl-methyl)-amine are obtained as colorless oil.

11.9 g (0.055 mol) of the above amine are dissolved in 40 ml dichlormethane and 4.2 ml (0.059 mol) acetylchloride are dropwise added. The mixture is stirred for 12 h at room temperature, washed with a solution of NaHCO$_3$, the organic phase dried over MgSO$_4$ and concentrated under vacuum. The residue is purified by chromatography over silica gel (hexane-ethylacetate 1:1). 9.65 g (68%) of the title amine are obtained as colorless oil. $^1$H-NMR (CDCl$_3$), δ (ppm), (Auswahl): 7.44 bm (NH), 3.84 dd (2H), 3.17 m (2H), 2.11 s (3H)

To a solution of 1.0 g (0.0039 mol) of the above amine in 6 ml ethylacetate at 10° C. a solution of 1.43 g m-chlorperbenzoic acid (0.0058 mol) in 3 ml ethylacetate are dropwise added. The mixture is stirred for 4 h at room temperature, washed with a solution of NaHCO$_3$, the organic phase is dried over MgSO$_4$ and concentrated under vacuum. The residue is purified by chromatography over silica gel (hexane-ethylacetate 2:1). 0.65 g (61%) of the title notroxide are obtained as red oil.

Elemental analysis calculated for C$_{13}$H$_{25}$N$_2$O$_4$: C 57.12%; H 9.22%; N 10.25%. Found: C 56.93%; H 9.28%; N 10.10%.

EXAMPLE A7

Preparation of (dimethyl-ethoxymethyl-methyl)-(dimethyl-ethoxycarbonyl-methyl)-amine-N-oxyl (107)

Preparation of (dimethyl-ethoxymethyl-methyl)-(dimethyl-ethoxycarbonyl-methyl)-amine 39.45 g (0.2 mol) of the sodium salt of N-(dimethyl-hydroxymethyl-methyl)-2-amino-isobutyric acid (prepared according to J. T. Lai.: Synthesis 122 (1984)) are dissolved in 200 ml dimethylformamide and 8.8 g (0.22 mol) sodium hydride (60% in parafin) are added in portions. After 12 h stirring at 20° C. the mixture is diluted with 500 ml water and extracted with toluene-hexane. The combined extracts are washed with water, dried over MgSO$_4$ and concentrated under vacuum. The residue is purified by chromatography over silica gel (hexane/ethylacetate 8:1). 25.3 g (55%) of the amine are obtained as colorless oil.

$^1$H-NMR (CDCl$_3$), δ (ppm): 4.13 q (2H), 3.47q (2H), 3.14 s (2H), 2.31 bs (NH), 1.35 s (6H), 1.29 t (3H), 1.17 t (3H), 1.08 s (6 H).

To a solution of 0.9 g sodium carbonate, 0.3 g sodium wolframate, 9 ml H$_2$O$_2$ 30% in 6 ml water a solution of 3 g (0.013 mol) (dimethyl-ethoxymethyl-methyl)-(dimethyl-ethoxycarbonyl-methyl)-amine in 15 ml methanol is added dropwise at 20° C. After 22 h stirring at 20° C. the red mixture is diluted with 50 ml water and extracted with ethylacetate-hexane. The combined extracts are washed with a saturated NaCl solution, dried over MgSO$_4$ and concentrated under vacuum. The residue is purified by chromatography over silica gel (hexane-ethylacetate 4:1). 2.75 g (86%) of the title compound are obtained as red oil.

Elemental analysis calculated for C$_{12}$H$_{24}$NO$_4$: C 58.51%; H 9.82%; N 5.69%. Found: C 58.54%; H 9.23%; N 5.85%.

EXAMPLE A8

Preparation of tert-butyl-(tert-butylaminocarbonyl-cyclopentyliden-methyl)-amine-N-oxyl (108)

Preparation of tert-butyl-(tert-butylaminocarbonyl-cyclopentyliden-methyl)-amine The title compound is prepared from t-butylamine, cyclopentanone, chloroform and NaOH in 15% yield in analogy to J. T. Lai, J. Org. Chem. 45, 3671 (1980).

m.p. 80–83° C.

Elemental analysis calculated for $C_{14}H_{28}N_2O$: C 69.95%; H 11.74%; N 11.65%. Found: C 69.81%; H 11.70%; N 11.85%.

Oxidation to the Corresponding Nitroxide

To a solution of 5.95 g (0.025 Mol) tert-butyl-(tert-butylaminocarbonyl-cyclopentyliden-methyl)-amine in 20 ml methanol 0.5 g sodiumcarbonate and 0.15 g sodiumwofframate are added. 8.6 ml of 35% hydrogen peroxid are added at 20° C. The mixture is stirred for 16 h at 20° C. 50 ml water are added and the red mixture is extracted with hexane-methyl-t-butyl ether. The extracts are washed with staurated NaCl solution, dried over $MgSO_4$ and concentrated under vacuum. The residue is purified by chromatography on silica gel (Hexan-Ethylactat 9:1). 2.63 g (39%) of the title compound are obtained with a m.p. of 84–90° C.

Elemental analysis calculated for $C_{14}H_{27}N_2O_2$: C 65.84%; H 10.66%; N 10.97%. Found: C 65.86%; H 10.55%; N 10.98%.

EXAMPLE A9

Preparation of bis-(dimethyl-benzoyloxymethyl-methyl)-amine-N-oxyl (109)

A) Preparation of bis-dimethyl-benzoyloxymethyl-methyl)amine 8.1 g (0.05 mol) bis-(dimethyl-hydroxymethyl-methyl)-amine (prepared according to L. T. Lai,: Synthesis 122 (1984)) are dissolved in 80 ml dichloromethane and 14.41 g (0.102 mol) benzoylchloride are added. The mixture is stirred for 12 h at room temperature and washed with $NaHCO_3$ solution. The organic phase is dried over MgSO4 and concentrated under vaccum. The residue is purified by chromatography over silica gel (hexane-ethylacetate 2:1). 9.3 g (50,4%) of the title compound are obtained as colorless oil.

$^1$H-NMR (300 MHz, $CDCl_3$), δ (ppm): 8.1–7.3 m (10H arom.), 4.16 s (4H), 1.32 s (12H).

B) To a solution of 10.3 g (0.028 mol) bis-(dimethyl-benzoyloxymethyl-methyl)-amine in 120 ml ethylacetate at 10° C. a solution of 10.3 g (0.042 mol) m-chlorperbenzoic acid in 30 ml ethylacetate is dropwise added. The mixture is stirred for 2 h at room temperature, washed with a $NaHCO_3$ solution, the organic phase dried over MgSO4 and concentrated under vaccum. The residue is purified by chromatography over silica gel (hexane-ethylacetate 4:1). 6.6 g (62%) of the title compound are obtained as red solid. M.p. 62–63° C.

Elemental analysis calculated for $C_{22}H_{26}NO_5$: C 68.73%, H 6.82%, N 3.64%. Found: C 68.88%, H 6.72%, N 3.69%.

EXAMPLE A10

Preparation of N-(cyano-isopropyloxy)-tert-butyl-(dimethyl-methylaminocarbonyl-methyl)-amine (201)

6.0 g (0.032 mol) nitroxide (101) and 3.42 g (0.021 mol) azobisisobutyronitrile are refluxed in 15 ml benzene under nitrogen atmosphere for 3 h. The solvent is evaporated and the residue purified by chromatography over silica gel (ethylacetate-hexane 1:1). After recrystallisation from hexane 3.95 g (54%) of the title compound (201) are obtained with a m.p. of 96–101° C.

Elemental analysis calculated for $C_{13}H_{25}N_3O_2$: C 61.15%; H 9.87%; N 16.46%. Found: C 61.07%; H 9.58%; N 16.55%.

EXAMPLE A11

Preparation of N-(cyano-isopropyloxy)-tert-butyl-(dimethyl-tert-butylaminocarbonyl-methyl)-amine (202)

The compound is prepared in analogy to example A8 from compound 102 and azobis-isobutyronitrile. Yield: 72.5%, m.p. 77–79° C.

Elemental analysis calculated for $C_{16}H_{31}N_3O_2$: C 64.61%; H 10.50%; N 14.13%. Found: C 64.65%; H 10.42%; N 14.33%.

EXAMPLE A12

Preparation of N-(cyano-cyclohexyloxy)-tert-butyl-(dimethyl-tert-butylaminocarbonyl-methyl)-amine (203)

The compound is prepared in analogy to example A8 from the nitroxide (102) and azobis-(cyclohexancarbonitrile) in chlorbenzene at 100° C. in a yield of 43% as colorless oil.

$^1$H-NMR ($CDCl_3$), δ (ppm): 6.96 (NH), 2.42–2.31 m (2H), 1.9–1.2 m (8H), 1.44 s (3H), 1.36 s (12 H), 1.33 s (9H).

EXAMPLE A13

Preparation of N-allyloxy-tert-butyl-(dimethyl-tert-butylaminocarbonyl-methyl)-amine (204)

Preparation of tert-butyl-(dimethyl-tert-butylaminocarbonyl-methyl)-hydroxylamine 46.4 g (0.2 mol) of nitroxide (102) in 150 ml methanol over 0.3 g $PtO_2$ are hydrogenated at room temperature under normal pressure. After hydrogen uptake is completed, the catalyst is removed and methanol is evaporated. The solud residue is suspended in hexane, the crystals are sucked off and washed. 43.3 g (94%) of the title hydroxylamine are obtained m.p. 165–168° C.

Elemental analysis calculated for $C_{12}H_{26}N_2O_2$: C 62.57%; H 11.38%; N 12.16%. Found: C 62.57%; H 11.38%; N 12.19%.

To 4.6 g (0.020 mol) of the above hydroxylamine in 16 ml dimethylformamide 0.96 g (0.022 mol) sodium hydride (55% in parrafin) are added in portions. After 1 h stirring at room temperature 2.7 g (0.022 mol) Allylbromide are dropwise added and the mixture is stirred over night. The mixture is poured into 100 ml water and extracted with methyl-tert-butylether. The combined extracts are washed with saturated NaCl solution, dried over $MgSO_4$ and concentrated under vacuum. The residue is purified by chromatography over silica gel (hexane-ethylacetate 9:1). 4.65 g (86%) of the title compound (204) are obtained as colorless oil.

Elemental analysis calculated for $C_{15}H_{30}N_2O_2$: C 66.63%; H 11.18%; N 10.36%. Found: C 66.73%; H 11.09%; N 10.21%.

EXAMPLE A14

Preparation of N-(2.4-pentadienyloxy)-tert-butyl-(dimethyl-tert-butylaminocarbonyl-methyl)-amine (205)

The compound is prepared in analogy to compound 204 from tert-butyl-(dimethyl-tert-butylaminocarbonyl-methyl)-hydroxylamine and 1-brom-2,4-pentadien in 80% yield as colorless oil.

$^1$H-NMR ($CDCl_3$), δ (ppm): 6.73 (NH), 6.41–6.21 m (1H), 5.80–5.71 m (1H), 5.26–5.11 m (2H), 4.36 d (2H), 1.40 s (3H), 1.34 s (12 H), 1.21 s (9H).

EXAMPLE A15

Preparation of N-methallyloxy-tert-butyl-(dimethyl-tert-butylaminocarbonyl-methyl)-amine (206)

The compound is prepared in analogy to compound (204) from tert-butyl-(dimethyl-tert-butylaminocarbonyl-methyl)-hydroxylamine and methallylchloride in 84% yield as colorless oil.

Elemental analysis calculated for $C_{16}H_{32}N_2O_2$: C 67.56%; H 11.34%; N 9.85%. Found: C 67.56%; H 11.18%; N 9.83%.

EXAMPLE A16

Preparation of N-propargyloxy-tert-butyl-(dimethyl-tert-butylaminocarbonyl-methyl)-amine (207)

The compound is prepared in analogy to compound (204) from tert-butyl-(dimethyl-tert-butylaminocarbonyl-methyl)-hydroxylamine and propargylbromide in 78% yield as colorless oil.

$^1$H-NMR (CDCl$_3$), δ (ppm): 6.60 (NH), 4.73 d (2H), 2.51 t (1H), 1.41 s (3H), 1.34 s (12 H), 1.22 s (9H).

EXAMPLE A17

Preparation of N-benzyloxy-tert-butyl-(dimethyl-tert-butylaminocarbonyl-methyl)-amine (208)

The compound is prepared in analogy to compound (204) from tert-butyl-(dimethyl-tert-butylaminocarbonyl-methyl)-hydroxylamine and benzylbromide in 92% yield as colorless oil. Elemental analysis calculated for $C_{19}H_{32}N_2O_2$: C 71.21%; H 10.06%; N 8.74%. Found: C 71.22%; H 10.07%; N 8.94%.

EXAMPLE A18

Preparation of N-(2-tetrahydropyranyloxy)-tert-butyl-(dimethyl-tert-butylaminocarbonyl-methyl)-amine (209)

The compound is prepared in analogy to compound (204) from tert-butyl-(dimethyl-tert-butylaminocarbonyl-methyl)-hydroxylamine and 2-chlor-tetrahydropyrane in 33% yield as colorless oil.

$^1$H-NMR (CDCl$_3$), δ (ppm): 6.60 (NH), 4.81 m (1H), 3.96 m (1H), 3.54 m (1H), 1.8–1.1 m (6H), 1.33 s (24H).

EXAMPLE A19

Preparation of N-(Cyano-isopropyloxy)-tert-butyl-(dimethyl-n-butylaminocarbonyl-methyl)-amine (210)

The compound is prepared in analogy to compound (201) from the nitroxide (103) and azobisisobutyronitrile in 48% yield as colorless oil.

$^1$H-NMR (CDCl$_3$), δ (ppm): 6.95 (NH), 3.24 m (2H), 1.80 s (3H), 1.72 s (3H), 1.70–1.30 m (4H), 1.45 s (3H), 1.38 s (3H), 1.30 s (9H), 0.93 t (3H).

EXAMPLE A20

Preparation of N-(cyano-cyclohexyloxy)-tert-butyl-(dimethyl-n-butylaminocarbonyl-methyl)-amine (211)

The compound is prepared in analogy to compound (201) from the nitroxide (103) and azobis(cyclohexanecarbonitrile) in chlorbenzene at 100°0 C. in 53% yield as colorless oil.

$^1$H-NMR (CDCl$_3$), δ (ppm): 7.04 (NH), 3.24 m (2H), 2.35 m (2H), 1.9–1.2 m (12H), 1.45 s (3H), 1.38 s (3H), 1.30 s (9H), 0.93 t (3H).

EXAMPLE A21

Preparation of N-(cyano-isopropyloxy)-tert-butyl-(dimethyl-methoxycarbonyl-methyl)-amine (212)

The compound is prepared in analogy to compound (201) from the nitroxide (104) and azobisisobutyronitrile in 24% yield with a m.p. of 78–85°C.

Elemental analysis calculated for $C_{13}H_{24}N_2O_3$: C 60.91%; H 9.44%; N 10.93%. Found: C 60.60%; H 9.26%; N 10.73%.

EXAMPLE A22

Preparation of N-(2-phenylethyloxy)-bis-(dimethyl-acetoxymethyl-methyl)-amine (213)

In reactor suitable for photo reactions, 150 ml ethylbenzene, 5,7 g (0,022 mol) nitroxide (105) and 13,5 g (0,092 mol) t-butylperoxide are mixed. The red solution is purged with nitrogen and subsequent exposed to a mercury immersion lamp under nitrogen atmosphere at 20–25° C. After 4 h a colorless solution is obtained. The reaction mixture is concentrated under vacuum and purified by chromatography over silica gel (hexane-ethylacetate 2:1). 7.2 g (90%) of the title compound are obtained as yellowish liquid.

Elemental analysis calculated for $C_{20}H_{31}NO_5$: C 65.73%; H 8.55%; N 3.83%. Found: C 65.94%; H 8.61%; N 3.84%.

EXAMPLE A23

Preparation of N-(cyano-isopropyloxy)-(dimethyl-ethoxymethyl-methyl)-(dimethyl-ethoxycarbonyl-methyl)-amine (214)

The compound is prepared in analogy to compound (201) from the nitroxide (107) and azobisisobutyronitrile in 44% yield as colorless oil.

$^1$H-NMR (CDCl$_3$), δ (ppm): 4.18 m (2H), 3.60–3.20 m (4H), 1.90–1.10 m (24H).

EXAMPLE A24

Preparation of N-(2-phenylethoxy)bis-(dimethyl-benzoyloxymethyl-methyl-amine (215)

The compound is prepared in analogy to example A22 from the nitroxide (109) and ethylbenzene in 76% yield as colorless oil.

$^1$H-NMR (CDCl$_3$), δ (ppm): 8.1–7.3 m (15H arom.), 4.88 q (1H), 4.4 dxd (2H), 3.95 dxd (2H), 1.6–1.2 m (15H).

EXAMPLE A25

Preparation of N-diphenylmethyloxy-tert-butyl-(dimethyl-tert-butylamino-carbonyl-methyl)-amine (216)

The compound is prepared in analogy to example A13 from tert-butyl-(dimethyl-tert-butylaminocarbonyl-methyl)-hydroxylamine and diphenylmethylchloride in 62.7% yield as colorless crystals, m.p. 89–92° C.

$^1$H-NMR (300 MHz, CDCl$_3$), δ (ppm): 7.38–7.22 m (10H), 6.68 bs (NH), 5.72 s (1H), 1.34 s (12H), 1.13 s (9H), 0.92 s (3H).

The compounds prepared in examples A10 to A25 are summarized in Table 2.

TABLE 2

| Nr | Struktur |
|---|---|
| 201 | (structure) |
| 202 | (structure) |
| 203 | (structure) |
| 204 | (structure) |
| 205 | (structure) |
| 206 | (structure) |
| 207 | (structure) |

TABLE 2-continued

| Nr | Struktur |
|---|---|
| 208 | (structure) |
| 209 | (structure) |
| 210 | (structure) |
| 211 | (structure) |
| 212 | (structure) |
| 213 | (structure) |
| 214 | (structure) |

TABLE 2-continued

| Nr | Struktur |
|---|---|
| 215 | |
| 216 | |

B) POLYMERIZATIONS USING COMPOUNDS OF TABLE 2 AS INITIATORS

General Remarks

Solvents and monomers are distilled over a Vigreux column under argon atmosphere or under vacuum, shortly before being used.

To remove oxygen all polymerization reaction mixtures are flushed before polymerization with argon and evacuated under vaccum applying a freeze-thaw cycle. The reaction mixtures are then polymerized under argon atmosphere.

At the start of the polymerization reaction, all starting materials are homogeneously dissolved.

Conversion is determined by removing unreacted monomers from the polymer at 80° C. and 0.002 torr for 30 minutes, weighing the remaining polymer and subtracting the weight of the initiator.

Characterization of the polymers is carried out by MALDI-MS (Matrix Assisted Laser Desorption Ionization Mass Spectrometry) and/or GPC (Gel Permeation Chromatography).

MALDI-MS

Measurements are performed on a linear TOF (Time Of Flight) MALDI-MS LDI-1700 Linear Scientific Inc., Reno, USA. The matrix is 2,5-dihydroxybenzoic acid and the laser wavelength is 337 nm.

GPC

Is performed using RHEOS 4000 of FLUX INSTRUMENTS. Tetrahydrofurane (THF) is used as a solvent and is pumped at 1 ml/min. Two chromatography columns are put in series: type Plgel 5 µm mixed-C of POLYMER INSTRUMENTS, Shropshire, UK. Measurements are performed at 40° C. The columns are calibrated with low polydispersity polystyrenes having Mn from 200 to 2 000 000 Dalton. Detection is carried out using a RI-Detector ERC-7515A of ERCATECH AG at 30° C.

EXAMPLE B1

Polymerization of n-butylacrylate using Compound 201 at 145° C.

In a 50 ml three neck flask, equipped with thermometer, cooler and magnetic stirrer, 597 mg (2.34 mmol) of compound 201 and 20 g (156 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 14.8 g (74%) of the initial monomer have reacted. A clear colorless viscous fluid is obtained.

GPC: Mn=6200, Mw=11000, Polydispersity (PD)=1.8

EXAMPLE B2

Polymerization of n-butylacrylate using compound 202 at 130° C.

In a 50 ml three neck flask, equipped with thermometer, cooler and magnetic stirrer, 696 mg (2.34 mmol) of compound 202 and 20 g (156 mmol) of n-butylacrylate are mixed and degased. The clear solution obtained is heated under argon to 130° C. and polymerization is carried out during 5 h. The reaction mixture is then cooled to 60° C. The remaining monomer is removed by evaporation under high vacuum. 6 g (30%) of the initial monomer have reacted. A clear colorless viscous fluid is obtained.

GPC: Mn=2600, Mw=4000, Polydispersity (PD)=1.5

EXAMPLE B3

Polymerization of n-butylacrylate using Compound 202 at 145° C.

In a 50 ml three neck flask, equipped with thermometer, cooler and magnetic stirrer, 696 mg (2.34 mmol) of compound 202 and 20 g (156 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 17.8 g (89%) of the initial monomer have reacted. A clear colorless viscous fluid is obtained.

GPC: Mn=6600, Mw=12300, Polydispersity (PD)=1.9

EXAMPLE B4

Polymerization of n-butylacrylate using Compound 204 at 145° C.

In a 50 ml three neck flask, equipped with thermometer, cooler and magnetic stirrer, 633 mg (2.34 mmol) of compound 204 and 20 g (156 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 13.6 g (68%) of the initial monomer have reacted. A clear colorless viscous fluid is obtained.

GPC: Mn=6000, Mw=10200, Polydispersity (PD)=1.7

EXAMPLE B5

Polymerization of n-butylacrylate using Compound 204 and 12.8% dicumylperoxide at 130° C.

In a 50 ml three neck flask, equipped with thermometer, cooler and magnetic stirrer, 633 mg (2.34 mmol) of compound 204, 95 mg (0.3 mmol) dicumylperoxide and 15 g (117 mmol) of n-butylacrylate are mixed and degased. The clear solution obtained is heated under argon to 130° C. and polymerization is carried out during 5 h. The reaction mixture is then cooled to 60° C. The remaining monomer is removed by evaporation under high vacuum. 12.75 g (85%) of the initial monomer have reacted. A clear colorless viscous fluid is obtained.

GPC: Mn=6000, Mw=12200, Polydispersity (PD)=2.1

EXAMPLE B6

Polymerization of n-butylacrylate using Compound 204 and 8.5% dicumylperoxide at 130° C.

In a 50 ml three neck flask, equipped with thermometer, cooler and magnetic stirrer, 633 mg (2.34 mmol) of compound 204, 63 mg (0.2 mmol) dicumylperoxide and 15 g (117 mmol) of n-butylacrylate are mixed and degased. The clear solution obtained is heated under argon to 130° C. and polymerization is carried out during 5 h. The reaction mixture is then cooled to 60° C. The remaining monomer is removed by evaporation under high vacuum. 10.95 g (73%) of the initial monomer have reacted. A clear colorless viscous fluid is obtained.

GPC: Mn=5000, Mw=9200, Polydispersity (PD)=1.8

EXAMPLE B7

Polymerization of n-butylacrylate using Compound 204 and 4.3% dicumylperoxide at 130° C.

In a 50 ml three neck flask, equipped with thermometer, cooler and magnetic stirrer, 633 mg (2.34 mmol) of compound 204, 31 mg (0.1 mmol) dicumylperoxide and 15 g (117 mmol) of n-butylacrylate are mixed and degased. The clear solution obtained is heated under argon to 130° C. and polymerization is carried out during 5 h. The reaction mixture is then cooled to 60° C. The remaining monomer is removed by evaporation under high vacuum. 8.5 g (54%) of the initial monomer have reacted. A clear colorless viscous fluid is obtained.

GPC: Mn=3900, Mw=6500, Polydispersity (PD)=1.6

EXAMPLE B8

Polymerization of n-butylacrylate using Compound 206 at 145° C.

In a 50 ml three neck flask, equipped with thermometer, cooler and magnetic stirrer, 326 mg (1.1mmol) of compound 206 and 10 g (78 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 7.1 g (71%) of the initial monomer have reacted. A clear colorless viscous fluid is obtained.

GPC: Mn=5700, Mw=11000, Polydispersity (PD)=1.9

EXAMPLE B9

Polymerization of n-butylacrylate using Compound 207 at 145° C.

In a 50 ml three neck flask, equipped with thermometer, cooler and magnetic stirrer, 616 mg (2.34 mmol) of compound 207 and 20 g (156 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 17.8 g (89%) of the initial monomer have reacted. A clear colorless viscous fluid is obtained. GPC: Mn =7800, Mw=16200, Polydispersity (PD)=2.1

EXAMPLE B10

Polymerization of n-butylacrylate using Compound 208 at 145° C.

In a 50 ml three neck flask, equipped with thermometer, cooler and magnetic stirrer, 368 mg (1.1 mmol) of compound 208 and 10 g (78 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 8.5 g (91%) of the initial monomer have reacted. A clear colorless viscous fluid is obtained.

GPC: Mn=6500, Mw=14700, Polydispersity (PD)=2.3

EXAMPLE B11

Polymerization of n-butylacrylate using Compound 210 at 145° C.

In a 50 ml three neck flask, equipped with thermometer, cooler and magnetic stirrer, 683 mg (2.34 mmol) of compound 210 and 20 g (156 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 15.7 g (79%) of the initial monomer have reacted. A clear colorless viscous fluid is obtained.

GPC: Mn=5800, Mw=10500, Polydispersity (PD)=1.8

EXAMPLE B12

Polymerization of n-butylacrylate using Compound 21 at 145° C.

In a 50 ml three neck flask, equipped with thermometer, cooler and magnetic stirrer, 790 mg (2.34 mmol) of compound 211 and 20 g (156 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 17 g (89%) of the initial monomer have reacted. A clear colorless viscous fluid is obtained.

GPC: Mn=5400, Mw=9200, Polydispersity (PD)=1.7

EXAMPLE B13

Polymerization of n-butylacrylate using Compound 212 at 145° C.

In a 50 ml three neck flask, equipped with thermometer, cooler and magnetic stirrer, 599 mg (2.34 mmol) of compound 212 and 20 g (156 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 18 g (90%) of the initial monomer have reacted. A clear colorless viscous fluid is obtained.

GPC: Mn=4600, Mw=10000, Polydispersity (PD)=2.2

EXAMPLE B14

Polymerization of n-butylacrylate using Compound 216 at 145° C.

In a 50 ml three neck flask, equipped with thermometer, cooler and magnetic stirrer, 926 mg (2.34 mmol) of compound 216 and 20 g (156 mmol) of n-butylacrylate are mixed and degased. The clear solution obtained is heated under argon to 145° C. and polymerization is carried out during 5h. The reaction mixture is then cooled to 60° C. The remaining monomer is removed by evaporation under high vacuum. 18 g (90%) of the initial monomer have reacted. A clear yellow viscous fluid is obtained.

GPC: Mn=4600, Mw=8200, Polydispersity=1.7

What is claimed is:

1. A compound of formula (Ib) or (Ic)

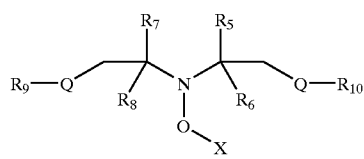

(Ib)

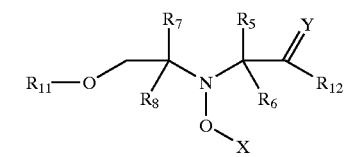

(Ic)

wherein in formula (Ib)

Q is O;

$R_5$, $R_6$, $R_7$ and $R_8$ are independently of each other $C_1$–$C_{10}$alkyl, $C_5$–$C_{12}$cycloalkyl; or $R_5$ and $R_6$ and/or $R_7$ and $R_8$ together with the carbon atom form a $C_5$–$C_{12}$cycloalkyl ring; and $R_9$ and $R_{10}$ are independently of each other formyl, $C_2$–$C_{18}$alkylcarbonyl, benzoyl, $C_1$–$C_{18}$alkyl, benzyl or phenyl; and wherein in formula (Ic)

Y is O $R_5$, $R_6$, $R_7$ and $R_8$ are independently of each other $C_1$–$C_{10}$alkyl, $C_5$–$C_{12}$cycloalkyl; or $R_5$ and $R_6$ and/or $R_7$ and $R_8$ together with the carbon atom form a $C_5$–$C_{12}$cycloalkyl ring;

$R_{11}$ is formyl, $C_2$–$C_{18}$alkylcarbonyl, benzoyl, $C_1$–$C_{18}$alkyl, benzyl or phenyl; and $R_{12}$ is OH, $C_1$14 $C_{18}$alkoxy, benzyloxy, $NR_{23}R_{24}$, wherein $R_{23}$ and $R_{24}$ are independently of each other hydrogen, $C_1$–$C_{18}$alkyl or phenyl;

where

X represents a group having at least one carbon atom and is such that the free radical X. derived from X is capable of initiating polymerization of ethylenically unsaturated monomers.

2. A compound according to claim 1, wherein X is selected from the group consisting of —CH$_2$-aryl,

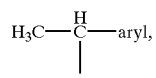

—CH$_2$—CH$_2$-aryl,

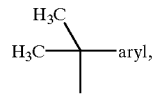

($C_5$–$C_6$cycloalkyl)$_2$CCN, ($C_1$–$C_{12}$alkyl)$_2$CCN, —CH$_2$CH=CH$_2$, ($C_1$–$C_{12}$)alkyl-CR$_{30}$—C(O)—($C_1$–$C_{12}$) alkyl, ($C_1$–$C_{12}$)alkyl-CR$_{30}$—C(O)—($C_6$–CR)aryl, ($C_1$–$C_{12}$) alkyl-CR$_{30}$—C(O)—($C_1$–$C_{12}$)alkoxy, ($C_1$–$C_{12}$)alkyl-CR$_{30}$—C(O)-phenoxy, ($C_1$–$C_{12}$)alkyl-CR$_{30}$—C(O)—N-di ($C_1$–$C_{12}$)alkyl, ($C_1$–$C_{12}$)alkyl-CR$_{30}$—CO—NH($C_1$–$C_{12}$) alkyl, ($C_1$–$C_{12}$)alkyl-CR$_{30}$—CO—NH$_2$, —CH$_2$CH=CH— CH$_3$, —CH$_2$—C(CH$_3$)=CH$_2$, —CH$_2$—CH=CH-phenyl,

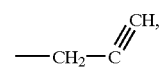

($C_1$–$C_{12}$)alkyl-CR$_{30}$—CN,

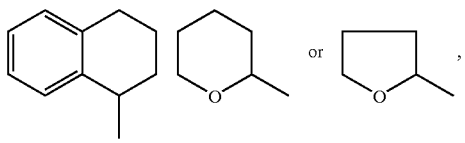

wherein $R_{30}$ is hydrogen or $C_1$–$C_{12}$alkyl;

the aryl groups are phenyl or naphthyl, which are unsubstituted or substituted with $C_1$–$C_{12}$alkyl, halogen, $C_1$–$C_{12}$alkoxy, formyl, $C_2$–$C_{12}$alkylcarbonyl, glycidyloxy, OH, —COOH or —COOC$_1$–$C_{12}$alkyl.

3. A compound according to claim 1, wherein X is selected from the group consisting of —CH$_2$-phenyl, CH$_3$CH-phenyl, (CH$_3$)$_2$C-phenyl, ($C_5$–$C_6$cycloalkyl)$_2$CCN, (CH$_3$)$_2$CCN, —CH$_2$CH=CH$_2$, CH$_3$CH—CH=CH$_2$(C$_1$14 C$_8$alkyl)CR$_{30}$—C(O)-phenyl, ($C_1$–$C_8$)alkyl-CR$_{30}$—C(O)— ($C_1$–$C_8$)alkoxy, ($C_1$–$C_8$)alkyl-CR$_{30}$—C(O)—($C_1$–$C_8$)alkyl, ($C_1$–$C_8$)alkyl-CR$_{30}$—C(O)—N—di($C_1$–$C_8$)alkyl, $C_1$–$C_8$) alkyl-CR$_{30}$—C(O)—NH($C_1$–$C_8$)alkyl, ($C_1$–$C_8$)alkyl-CR$_{30}$—C(O)—NH$_2$, wherein $R_{30}$ is hydrogen or ($C_1$–$C_8$) alkyl.

4. A compound according to claim 1, wherein X is selected from the group consisting of —CH$_2$-phenyl, CH$_3$CH-phenyl, (CH$_3$)$_2$C-phenyl, ($C_5$–$C_6$cycloalkyl)$_2$CCN, (CH$_3$)$_2$CCN, —CH$_2$CH=CH$_2$, CH$_3$CH—CH=CH$_2$ ($C_1$–$C_4$alkyl)CR$_{30}$—C(O)-phenyl, ($C_1$–$C_4$)alkyl-CR$_{30}$—C (O)—($C_1$–$C_4$)alkoxy, ($C_1$–$C_4$)alkyl-CR$_{30}$—C(O)—($C_1$–$C_4$) alkyl, ($C_1$–$C_4$)alkyl-CR$_{30}$—C(O)—N-di($C_1$–$C_4$)alkyl, ($C_1$–$C_4$)alkyl-CR$_{30}$—C(O)—NH($C_1$–$C_4$)alkyl, ($C_1$–$C_4$) alkyl-CR$_{30}$—C(O)—NH$_2$, wherein $R_{30}$ is hydrogen or ($C_1$–$C_4$)alkyl.

5. A compound of formula (Ib) according to claim 1, wherein Q is O;

$R_5$, $R_6$, $R_7$ and $R_8$ are independently of each other methyl or ethyl; or $R_5$ and $R_6$ and/or $R_7$ and $R_8$ together with the carbon atom form a $C_5$–$C_6$cycloalkyl ring;

$R_9$ and $R_{10}$ are independently of each other formyl, $C_2$–$C_8$alkylcarbonyl, benzoyl, $C_1$–$C_8$alkyl, benzyl or phenyl.

6. A compound of formula (Ic) according to claim 1, wherein Y is O;

$R_5$, $R_6$, $R_7$ and $R_8$ are independently of each other methyl or ethyl; or $R_5$ and $R_6$ and/or $R_7$ and $R_8$ together with the carbon atom form a $C_5$–$C_6$cycloalkyl ring;

$R_{11}$ is formyl, $C_2$–$C_{18}$alkylcarbonyl, benzoyl, $C_1$–$C_{18}$alkyl, benzyl or phenyl and $R_{12}$ is OH, $C_1$–$C_{18}$alkoxy, benzyloxy, $NR_{23}R_{24}$, wherein $R_{23}$ and $R_{24}$ are independently of each other hydrogen or $C_1$–$C_{18}$alkyl.

7. A polymerizable composition, comprising
a) at least one ethylenically unsaturated monomer or oligomer, and
b) at least one compound of formula (Ia), (Ib) or (Ic)

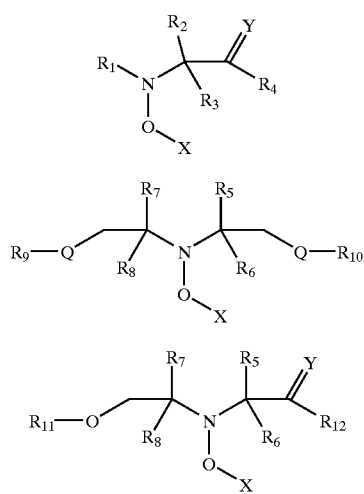

wherein

Y is O or $CH_2$;

Q is O or $NR_{20}$, wherein $R_{20}$ is hydrogen or $C_1$–$C_{18}$alkyl;

$R_1$ is tertiary $C_4$–$C_{18}$alkyl or phenyl, which are unsubstituted or substituted by halogen, OH, $COOR_{21}$ or C(O)—$R_{22}$ wherein $R_{21}$ is hydrogen, a alkali metal atom or $C_1$–$C_{18}$alkyl and $R_{22}$ is $C_1$–$C_{18}$alkyl; or $R_1$ is $C_5$–$C_{12}$cycloalkyl, $C_5$–$C_{12}$cycloalkyl which is interrupted by at least one O or N atom, a polycyclic alkyl radical or a polycyclic alkyl radical which is interrupted by at least one O or N atom;

$R_2$ and $R_3$ are independently $C_1$–$C_{18}$alkyl, benzyl, $C_5$–$C_{12}$cycloalkyl or phenyl, which are unsubstituted or substituted by halogen, OH, $COOR_{21}$ or C(O)—$R_{22}$ or together with the carbon atom form a $C_5$–$C_{12}$cycloalkyl ring;

if Y is O, $R_4$ and $R_{12}$ are OH, O(alkali-metal) $C_1$–$C_{18}$alkoxy, benzyloxy, $NR_{23}R_{24}$, wherein $R_{23}$ and $R_{24}$ are independently from each other hydrogen, $C_1$–$C_{18}$alkyl or phenyl, which are unsubstituted or substituted by halogen, OH, $COOR_{21}$ or C(O)—$R_{22}$;

if Y is $CH_2$, $R_4$ is OH, $C_1$–$C_{18}$alkoxy, benzyloxy, O—C(O)—($C_1$–$C_{18}$)alkyl or $NR_{23}R_{24}$;

$R_{12}$ are a group C(O)$R_{25}$, wherein $R_{25}$ is OH, $C_1$–$C_{18}$alkoxy, benzyloxy, $NR_{23}N_{24}$, wherein $R_{23}$ and $R_{24}$ are independently from each other hydrogen, $C_1$–$C_{18}$alkyl or phenyl, which are unsubstituted or substituted by halogen, OH, $COOR_{21}$ or C(O)—$R_{22}$;

$R_5$, $R_6$, $R_7$ and $R_8$ are independently of each other $C_1$–$C_{18}$alkyl, $C_5$–$C_{12}$cycloalykyl or phenyl, with the proviso that not more than two are phenyl; or $R_5$ and $R_6$ and/or $R_7$ and $R_8$ together with the carbon atom form a $C_5$–$C_{12}$cycloalkyl ring;

$R_9$ and $R_{10}$ are independently of each other hydrogen, formyl, $C_2$–$C_{18}$alkylcarbonyl, benzoyl, $C_1$–$C_{18}$alkyl, $C_5$–$C_{12}$cycloalkyl, $C_5$–$C_{12}$cycloalkyl which is interrupted by at least one O or N atom, benzyl or phenyl which are unsubstituted or substituted by halogen, OH, $COOR_{21}$ or C(O)—$R_{22}$;

$R_{11}$, is formyl, $C_2$–$C_{18}$alkylcarbonyl, benzoyl, $C_1$–$C_{18}$alkyl, $C_5$–$C_{12}$cycloalkyl, $C_5$–$C_{12}$cycloalkyl which is interrupted by at least one O or N atom, benzyl or phenyl which are unsubstituted or substituted by halogen, OH, $COOR_{21}$ or C(O)—$R_{22}$; and X represents a group having at least one carbon atom and is such that the free radical X. derived from X is capable of initiating polymerization of ethylenically unsaturated monomers.

8. A composition according to claim 7, wherein the ethylenically unsaturated monomer or oligomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl)acrylic acidanhydrides, (alkyl)acrylic acid salts, (alkyl)acrylic esters, (meth)acrylonitriles, (alkyl)acrylamides, vinyl halides or vinylidene halides.

9. A composition according to claim 8 wherein the ethylenically unsaturated monomer is selected from the group consisting of ethylene, propylene, n-butylene, i-butylene, isoprene, 1,3-butadiene, α-$C_5$–$C_{18}$alkene, styrene, α-methyl styrene, p-methyl styrene and compounds of formula $CH_2=C(R_a)$—(C=Z)—$R_b$, wherein $R_a$ is hydrogen or $C_1$–$C_4$alkyl, $R_b$ is $NH_2$, $O^-(Me^+)$, glycidyl, unsubstituted $C_1$–$C_{18}$alkoxy, $C_2$–$C_{100}$alkoxy interrupted by at least one N and/or O atom, or hydroxy-substituted $C_1$–$C_{18}$alkoxy, unsubstituted $C_1$–$C_{18}$alkylamino, di($C_1$–$C_{18}$alkyl)amino, hydroxy-substituted $C_1$–$C_{18}$alkylamino or hydroxy-substituted di($C_1$–$C_{18}$alkyl)amino, —O—$CH_2$—$CH_2$—$N(CH_3)_2$ or —O—$CH_2$—$CH_2$—$N^+H(CH_3)_2An^-$, $An^-$ is a anion of a monovalent organic or inorganic acid, Me is a monovalent metal atom or the ammonium ion and Z is oxygen or sulfur.

10. A composition according to claim 9, wherein $R_a$ is hydrogen or methyl, $R_b$ is $NH_2$, gycidyl, unsubstituted or with hydroxy substituted $C_1$–$C_4$alkoxy, unsubstituted $C_1$–$C_4$alkylamino, di($C_1$–$C_4$alkyl)amino, hydroxy-substituted $C_1$–$C_4$alkylamino or hydroxy-substituted di($C_1$–$C_4$alkyl)amino; and Z is oxygen.

11. A composition according to claim 10, wherein the ethylenically unsaturated monomer is selected from the group consisting of styrene, methylacrylate, ethylacrylate, butylacrylate, isobutylacrylate, tert.butylacrylate, hydroxyethylacrylate, hydroxpropylacrylate, dimethylaminoethylacrylate, glycidylacrylates, methyl (meth)acylate, ethyl(methyl)acrylate, butyl(meth)acrylate, hydroxyethyl(meth)acrylate, hydroxypropyl(meth)acrylate, dimethylaminoethyl(meth)acrylate, glycidyl(meth)acrylates, acrylonitrile, acrylamide, methacrylamide and dimethylaminopropylmethacrylamide.

12. A composition according to claim 7, wherein the ethylenically unsaturated monomer is a mixture of a methacrylate and an acrylate.

13. A composition according to claim 7, wherein the initiator compound is present in an amount of from 0.1 mol-% to 30 mol-%, based on the monomer or monomer mixture.

14. A process for preparing an oligomer, a cooligomer, a polymer or a copolymer (block or random) by free radical polymerization of at least one ethylenically unsaturated monomer or oligomer, which comprises (co)polymerizing the monomer or monomers/oligomers in the presence of at least one initiator compound of formula (Ia), (Ib) or (Ic) according to claim 7 under reaction conditions capable of effecting scission of the O—C bond to form two free radicals, the radical .X being capable of initiating polymerization.

15. A process according to claim 14, wherein the scission of the O—C bond is effected by ultrasonic treatment, heating or exposure to electromagnetic radiation, ranging from γ to microwaves.

16. A process according to claim 14, wherein the scission of the O—C bond is effected by heating and takes place at a temperature of between 50° C. and 160° C.

17. A polymer or oligomer having attached at least one initiator group —X and at least one oxyamine group of formula (IIIa), (IIIb) or (IIIc)

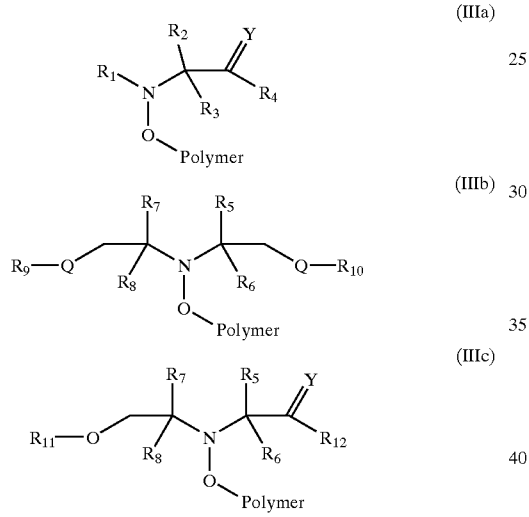

where $R_1$–$R_{12}$, Q and Y are as defined in claim 7.

18. A polymerizable composition, comprising a) at least one ethylenically unsaturated monomer or oligomer, b) a compound of formula (IIa), (IIb) or (IIc) and c) a radical iniator X. capable of initiating polymerization of ethylenically unsaturated monomers

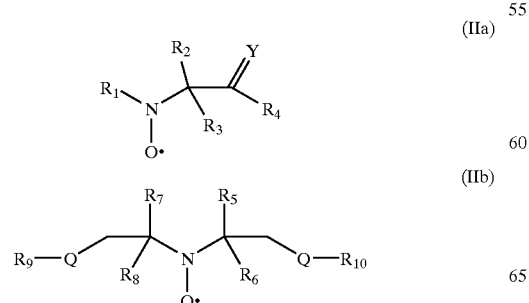

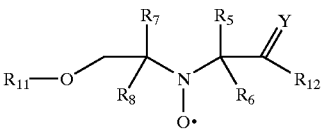

wherein

Y is O or $C_2$;

Q i O or $NR_{20}$, wherein $R_{20}$ is hydrogen or $C_1$–$C_{18}$alkyl;

$R_1$ is tertiary $C_4$–$C_{18}$alkyl or phenyl, which are unsubstituted or substituted by halogen, OH, $COOR_{21}$ or $C(O)$—$R_{22}$ wherein $R_{21}$ is hydrogen, a alkali metal atom or $C_1$–$C_{18}$alkyl and $R_{22}$ is $C_1$–$C_{18}$alkyl; or $R_1$ is $C_1$–$C_{12}$cycloalkyl, $C_5$–$C_{12}$cycloalkyl which is interrupted by at least one O or N atom, a polycyclic alkyl radical or a polycyclic alkyl radical which is interrupted by at least one O or N atom;

$R_2$ and $R_3$ are independently $C_1$–$C_{18}$alkyl, benzyl, $C_5$–$C_{12}$cycloalkyl or phenyl, which are unsubstituted or substituted by halogen, OH, $COOR_{21}$ or $C(O)$—$R_{22}$ or together with the carbon atom form a $C_5$–$C_{12}$cycloalkyl ring;

if Y is O, $R_4$ and $R_{12}$ are OH, O(alkali-metal) $C_1$–$C_{18}$alkoxy, benzyloxy, $NR_{23}R_{24}$, wherein $R_{23}$ and $R_{24}$ are independently from each other hydrogen, $C_1$–$C_{18}$alkyl or phenyl, which are unsubstituted or substituted by halogen, OH, $COOR_{21}$ or $C(O)$—$R_{22}$;

if Y is $CH_2$, $R_4$ is OH, $C_1$–$C_{18}$alkoxy, benzyloxy, O—C(O)—$(C_1$–$C_{18})$alkyl or $NR_{23}R_{24}$;

$R_{12}$ are a group $C(O)R_{25}$, wherein $R_{25}$ is OH, $C_1$–$C_{18}$alkoxy, benzyloxy, $NR_{23}R_{24}$, wherein $R_{23}$ and $R_{24}$ are independently from each other hydrogen, $C_1$–$C_{18}$alkyl or phenyl, which are unsubstituted or substituted by halogen, OH, $COOR_{21}$ or $C(O)$—$R_{22}$;

$R_5$, $R_6$, $R_7$ and $R_{18}$ are independently of each other $C_1$–$C_{18}$alkyl, $C_5$–$C_{12}$cycloalykyl or phenyl, with the proviso that not more than two are phenyl; or $R_5$ and $R_6$ and/or $R_7$ and $R_8$ together with the carbon atom form a $C_5$–$C_{12}$cycloalkyl ring;

$R_9$ and $R_{10}$ are independently of each other hydrogen, formyl, $C_2$–$C_{18}$alkylcarbonyl, benzoyl, $C_1$–$C_{18}$alkyl, $C_5$–$C_{12}$cycloalkyl, $C_5$–$C_{12}$cycloalkyl which is interrupted by at least one O or N atom, benzyl or phenyl which are unsubstituted or substituted by halogen, OH, $COOR_{21}$ or $C(O)$—$R_{22}$; and $R_{11}$ is formyl, $C_2$–$C_{18}$alkylcarbonyl, benzoyl, $C_1$–$C_{18}$alkyl, $C_5$–$C_{12}$cycloalkyl, $C_5$–$C_{12}$cycloalkyl which is interrupted by at least one O or N atom, benzyl or phenyl which are unsubstituted or substituted by halogen, OH, $COOR_{21}$ or $C(O)$—$R_{22}$.

19. A process for preparing an oligomer, a cooligomer, a polymer or a copolymer (block or random) by free radical polymerization, which comprises subjecting a composition according to claim 18 to heat or actinic radiation.

20. A polymerizable composition comprising a) at least one ethylenically unsaturated monomer or oligomer;

b) at least one compound of formula (Ia), (Ib) or (Ic) and c) at least one compound of formula (IIa), (IIb) or (IIc)

wherein said compounds are

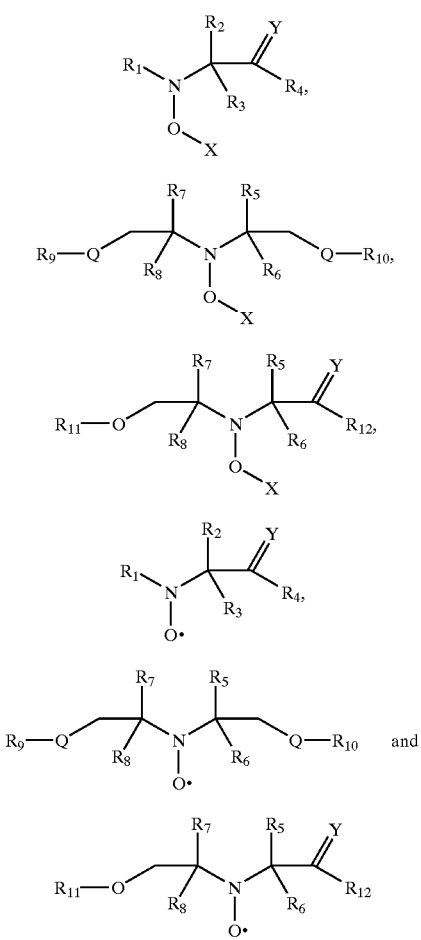

wherein
Y is O or $CH_2$;
Q is O or $NR_{20}$, wherein $R_{20}$ is hydrogen or $C_1$-$C_{18}$alkyl;
$R_1$ is tertiary $C_4$-$C_{18}$alkyl or phenyl, which are unsubstituted or substituted by halogen, OH, $COOR_{21}$ or C(O)—$R_{22}$ wherein $R_{21}$ is hydrogen, a alkali metal atom or $C_1$-$C_{18}$alkyl and $R_{22}$ is $C_1$-$C_{18}$alkyl; or $R_1$ is $C_5$-$C_{12}$cycloalkyl, $C_5$-$C_2$cycloalkyl which is interrupted by at least one O or N atom, a polycyclic alkyl radical or a polycyclic alkyl radical which is interrupted by at least one O or N atom;
$R_2$ and $R_3$ are independently $C_1$-$C_{18}$alkyl, benzyl, $C_5$-$C_{12}$cycloalkyl or phenyl, which are unsubstituted or substituted by halogen, OH, $COOR_{21}$ or C(O)—$R_{22}$ or together with the carbon atom form a $C_5$-$C_{12}$cycloalkyl ring;
if Y is O,
$R_4$ and $R_{12}$ are OH, O(alkali-metal) $C_1$-$C_{18}$alkoxy, benzyloxy, $NR_{23}R_{24}$, wherein $R_{23}$ and $R_{24}$ are independently from each other hydrogen, $C_1$-$C_{18}$alkyl or phenyl, which are unsubstituted or substituted by halogen, OH, $COOR_{21}$ or C(O)—$R_{22}$;
if Y is $CH_2$,
$R_4$ is OH, $C_1$-$C_{18}$alkoxy, benzyloxy, O—C(O)—($C_1$-$C_{18}$)alkyl or $NR_{23}R_{24}$;
$R_{12}$ are a group $C(O)R_{25}$, wherein $R_{25}$ is OH, $C_1$-$C_{18}$alkoxy, benzyloxy, $NR_{23}R_{24}$, wherein $R_{23}$ and $R_{24}$ are independently from each other hydrogen, $C_1$-$C_{18}$alkyl or phenyl, which are unsubstituted or substituted by halogen, OH, $COOR_{21}$ or C(O)—$R_{22}$;
$R_5$, $R_6$, $R_7$ and $R_8$ are independently of each other $C_1$-$C_{18}$alkyl, $C_5$-$C_{12}$cycloalykyl or phenyl, with the proviso that not more than two are phenyl; or $R_5$ and $R_6$ and/or $R_7$ and $R_8$ together with the carbon atom form a $C_5$-$C_{12}$cycloalkyl ring;
$R_9$ and $R_{10}$ are independently of each other hydrogen, formyl, $C_2$-$C_{18}$alkylcarbonyl, benzoyl, $C_1$-$C_{18}$alkyl, $C_5$-$C_{12}$cycloalkyl, $C_5$-$C_{12}$cycloalkyl which is interrupted by at least one O or N atom, benzyl or phenyl which are unsubstituted or substituted by halogen, OH, $COOR_{21}$ or C(O)—$R_{22}$;
$R_{11}$, is formyl, $C_2$-$C_{18}$alkylcarbonyl, benzoyl, $C_1$-$C_{18}$alkyl, $C_5$-$C_{12}$cycloalkyl, $C_5$-$C_{12}$cycloalkyl which is interrupted by at least one O or N atom, benzyl or phenyl which are unsubstituted or substituted by halogen, OH, $COOR_{21}$ or C(O)—$R_{22}$; and
X represents a group having at least one carbon atom and is such that the free radical X. derived from X is capable of initiating polymerization of ethylenically unsaturated monomers.

* * * * *